US012765948B2

(12) United States Patent
Feng et al.

(10) Patent No.: US 12,765,948 B2
(45) Date of Patent: Oct. 20, 2026

(54) METHODS FOR PATH PLANNING, AND METHODS, DEVICES, AND SYSTEMS FOR DETERMINING OPERATION GUIDANCE INFORMATION

(71) Applicant: SHANGHAI UNITED IMAGING HEALTHCARE CO., LTD., Shanghai (CN)

(72) Inventors: Juan Feng, Shanghai (CN); Le Yang, Shanghai (CN); Yang Hu, Shanghai (CN); Yange Ma, Shanghai (CN); Chenghang Han, Shanghai (CN); Yu Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 36 days.

(21) Appl. No.: 18/177,735

(22) Filed: Mar. 2, 2023

(65) Prior Publication Data

US 2023/0200910 A1 Jun. 29, 2023

Related U.S. Application Data

(63) Continuation of application No. PCT/CN2021/116258, filed on Sep. 2, 2021.

(30) Foreign Application Priority Data

Sep. 2, 2020 (CN) ........................ 202010912200.X
Sep. 22, 2020 (CN) ........................ 202011003191.9
Dec. 7, 2020 (CN) ........................ 202011418590.1

(51) Int. Cl.
*A61B 34/10* (2016.01)
*A61B 6/00* (2024.01)
(Continued)

(52) U.S. Cl.
CPC ............ *A61B 34/10* (2016.02); *A61B 6/4417* (2013.01); *A61B 6/5217* (2013.01);
(Continued)

(58) Field of Classification Search
CPC ................ A61B 6/4417; A61B 6/5247; A61B 6/5261; A61B 8/4416; A61B 8/5261;
(Continued)

(56) References Cited

U.S. PATENT DOCUMENTS 3,826,127 A * 7/1974 Molina .................. G01N 29/28 73/644
5,232,498 A * 8/1993 Hayakawa ............. G10K 11/02 118/244
(Continued)

FOREIGN PATENT DOCUMENTS

CA 2473963 A1 1/2005
CN 202875360 U 4/2013
(Continued)

OTHER PUBLICATIONS

International Search Report in PCT/CN2021/116258 mailed on Nov. 22, 2021, 5 pages.
(Continued)

*Primary Examiner* — Pascal M Bui Pho
*Assistant Examiner* — Nicholas A Robinson
(74) *Attorney, Agent, or Firm* — METIS IP LLC

(57) ABSTRACT

The present disclosure provides methods for path planning, and methods, devices, and systems for determining operation guidance information. The methods include obtaining an X-ray image of a target object, and marking a location of a lesion on the X-ray image of the target object; obtaining an ultrasonic image of the target object, and obtaining a fused image by fusing the ultrasonic image of the target object with the marked X-ray image; and obtaining a planned path
(Continued)

by performing a path planning based on a location of the lesion in the fused image. According to the methods provided herein, the problem that a single medical image providing relatively little information and without effective reference for surgery can now be solved. The surgical instrument can be implanted based on the planned path, thereby improving the success rate of surgery and reducing surgical complications.

15 Claims, 12 Drawing Sheets

(51) Int. Cl.

| | |
|---|---|
| ***A61B 8/00*** | (2006.01) |
| ***A61B 8/08*** | (2006.01) |
| ***A61B 34/20*** | (2016.01) |
| ***G06T 5/50*** | (2006.01) |
| ***G06T 7/00*** | (2017.01) |
| ***G06T 7/50*** | (2017.01) |
| ***G06T 7/70*** | (2017.01) |

(52) U.S. Cl.

CPC .......... *A61B 6/5247* (2013.01); *A61B 8/0841* (2013.01); *A61B 8/4416* (2013.01); *A61B 8/5261* (2013.01); *A61B 34/20* (2016.02); *G06T 5/50* (2013.01); *G06T 7/0012* (2013.01); *G06T 7/50* (2017.01); *G06T 7/70* (2017.01); *A61B 2034/107* (2016.02); *A61B 2034/2063* (2016.02); *G06T 2207/10116* (2013.01); *G06T 2207/10132* (2013.01); *G06T 2207/20221* (2013.01); *G06T 2207/30096* (2013.01)

(58) Field of Classification Search

CPC ....... A61B 34/20; A61B 34/10; A61B 6/5217; A61B 8/0841; A61B 2034/107; A61B 2034/2063; A61B 5/0035; A61B 5/7267; A61B 2090/364; A61B 2090/374; A61B 2090/376; A61B 2090/378; A61B 6/00; G06T 5/50; G06T 7/0012; G06T 7/50; G06T 7/70; G06T 2207/10116; G06T 2207/10132; G06T 2207/20221; G06T 2207/30096; G06T 7/00; G16H 30/40; G16H 50/20; G16H 50/70; G16H 20/40; G06N 3/044; G06N 3/0464; G06N 3/09

See application file for complete search history.

(56) References Cited

U.S. PATENT DOCUMENTS

| | | | | |
|---|---|---|---|---|
| 9,436,993 | B1 | 9/2016 | Stolka et al. | |
| 10,706,610 | B2 | 7/2020 | Kosmecki et al. | |
| 2002/0018588 | A1 * | 2/2002 | Kusch | A61B 6/4405 382/131 |
| 2003/0154201 | A1 * | 8/2003 | Berestov | G06T 17/05 |
| 2004/0106916 | A1 | 6/2004 | Quaid et al. | |
| 2007/0086659 | A1 * | 4/2007 | Chefd'hotel | G06V 10/757 382/225 |
| 2009/0141958 | A1 * | 6/2009 | Graumann | A61B 6/4441 382/132 |
| 2010/0166147 | A1 * | 7/2010 | Abenaim | A61B 8/0825 600/437 |
| 2011/0105900 | A1 * | 5/2011 | Entrekin | A61B 8/4455 600/443 |
| 2014/0073907 | A1 * | 3/2014 | Kumar | A61B 10/0241 600/407 |
| 2014/0180082 | A1 * | 6/2014 | Evans | A61B 6/502 600/436 |
| 2014/0225611 | A1 * | 8/2014 | Rapoport | G01R 33/465 324/309 |
| 2016/0249984 | A1 | 9/2016 | Janssen | |
| 2016/0317225 | A1 | 11/2016 | Girotto et al. | |
| 2017/0215969 | A1 | 8/2017 | Zhai et al. | |
| 2017/0309069 | A1 | 10/2017 | Thomas et al. | |
| 2018/0235701 | A1 | 8/2018 | Gerard et al. | |
| 2019/0247132 | A1 * | 8/2019 | Harks | A61B 8/461 |
| 2019/0251723 | A1 | 8/2019 | Coppersmith, III et al. | |
| 2021/0358119 | A1 * | 11/2021 | Vahala | G06T 11/006 |
| 2022/0165051 | A1 * | 5/2022 | Tokuyama | A22C 17/004 |
| 2023/0103969 | A1 * | 4/2023 | St. Pierre | G06T 7/0014 382/128 |

FOREIGN PATENT DOCUMENTS

| | | | | |
|---|---|---|---|---|
| CN | 103654809 | A | 3/2014 | |
| CN | 105193447 | A | 12/2015 | |
| CN | 105496433 | A | 4/2016 | |
| CN | 107358594 | A | 11/2017 | |
| CN | 107661122 | A | 2/2018 | |
| CN | 208098707 | U | 11/2018 | |
| CN | 109124764 | A | 1/2019 | |
| CN | 109745061 | A | 5/2019 | |
| CN | 109978915 | A | 7/2019 | |
| CN | 110151210 | A | 8/2019 | |
| CN | 110464459 | A | 11/2019 | |
| CN | 209629699 | U | 11/2019 | |
| CN | 110811676 | A | 2/2020 | |
| CN | 111354453 | A | 6/2020 | |
| CN | 111529063 | A * | 8/2020 | A61B 34/10 |
| CN | 211583228 | U | 9/2020 | |
| CN | 111728638 | A | 10/2020 | |
| CN | 112053346 | A | 12/2020 | |
| CN | 112057165 | A | 12/2020 | |
| CN | 112704506 | A | 4/2021 | |
| CN | 215191674 | U | 12/2021 | |
| DE | 102012203291 | A1 | 3/2013 | |
| EP | 1720038 | A2 | 11/2006 | |
| EP | 3669942 | A1 | 6/2020 | |
| WO | 2005083629 | A1 | 9/2005 | |
| WO | 2011074207 | A1 | 6/2011 | |
| WO | 2013018003 | A1 | 2/2013 | |
| WO | 2018112063 | A1 | 6/2018 | |
| WO | 2019149639 | A1 | 8/2019 | |

OTHER PUBLICATIONS

Written Opinion in PCT/CN2021/116258 mailed on Nov. 22, 2021, 9 pages.

First Office Action in Chinese Application No. 202011003191.9 mailed on May 21, 2021, 19 pages.

The Second Office Action in Chinese Application No. 202011003191.9 mailed on Dec. 17, 2021, 19 pages.

Communication pursuant to Article 94(3) EPC in European Application No. 21863665.2 mailed on Mar. 17, 2026, 9 pages.

* cited by examiner

METHODS FOR PATH PLANNING, AND METHODS, DEVICES, AND SYSTEMS FOR DETERMINING OPERATION GUIDANCE INFORMATION

CROSS-REFERENCE TO RELATED APPLICATIONS

This application is a Continuation of International Patent Application No. PCT/CN2021/116258, filed on Sep. 2, 2021, which claims priority of the Chinese Patent Application No. 202011418590.1, filed on Dec. 7, 2020, entitled "Detection Devices and Multimodal Medical Imaging Systems", the Chinese Patent Application No. 202011003191.9, filed on Sep. 22, 2020, entitled "Methods, Devices, Equipment, and Medium For Path Planning", and the Chinese Patent Application No. 202010912200.X, filed on Sep. 2, 2020, entitled "Methods and Systems for Determining Operation Guidance Information", the entire contents of which are hereby incorporated by reference in its entirety.

TECHNICAL FIELD

The present disclosure relates to the field of medical technology, and in particular to methods for path planning, and methods, devices and systems for determining operation guidance information.

BACKGROUND

In recent years, due to the complexity of surgery, it is necessary to use images to navigate surgical operations to improve the accuracy of the surgery.

In some spinal minimally invasive interventional operations and pain operations, such as sympathetic nerve block or small acupotomy therapy, clinical navigation of surgery may be performed using images acquired by an X-ray imaging device alone or images acquired by a mobile ultrasound device alone.

When the navigation is performed using the images acquired by the X-ray imaging device alone, performing the whole operation in perspective mode may bring certain radiation damage to doctors and patients, and the X-ray images may only present information of human bone tissues, and not image human blood vessels, or nerves, etc. Doctors may rely on experience to carry out surgery, greatly prolonging the operation time, and having problems such as low accuracy and high risk. When the navigation is performed using the images acquired by the mobile ultrasound device alone, due to the low resolution of ultrasonic images, doctors may not clearly see the subtle tissue structures through ultrasonic images. Besides, the field of view of ultrasonic images may be small and some anatomical structures may be highly similar, and thus the lesion may not be accurately identified through ultrasonic images.

SUMMARY

Accordingly, the present disclosure provides methods for path planning, and methods, devices, and systems for determining operation guidance information, to solve the problem that a single medical image provides relatively little information and cannot provide effective reference for surgery, and achieve the effect of improving the success rate of surgery and reducing surgical complications by planning the action path of surgical instruments.

The present disclosure provides a method for path planning. The method may comprise obtaining an X-ray image of a target object, and marking a location of a lesion on the X-ray image of the target object; obtaining an ultrasonic image of the target object, and obtaining a fused image by fusing the ultrasonic image of the target object with the marked X-ray image; and obtaining a planned path by performing a path planning based on a location of the lesion in the fused image.

In one embodiment, the method may further include obtaining operation guidance information associated with a target part, the target part including the location of the lesion.

The obtaining a planned path by performing a path planning based on a location of the lesion in the fused image may include obtaining the planned path by performing the path planning based on the operation guidance information associated with the target part and the location of the lesion in the fused image.

In one embodiment, the obtaining operation guidance information associated with a target part may include obtaining an optical image of the target object; obtaining target part information under a skin of the target object in a medical task; and determining the operation guidance information associated with the target part based on the optical image and the target part information.

In one embodiment, the obtaining target part information under a skin of the target object in a medical task may include obtaining a medical image of the target part under the skin of the target object.

The determining the operation guidance information associated with the target part based on the optical image and the target part information may include determining the operation guidance information by processing the optical image and the medical image based on a first preset algorithm.

In one embodiment, the method may further include determining indication information capable of being reflected on a surface of the target object through an indication device based on the operation guidance information.

In one embodiment, the method may further include outputting the operation guidance information through a terminal device.

In one embodiment, the first preset algorithm may include a machine learning model, and the determining the operation guidance information associated with the target part based on the optical image and the target part information may further include determining the operation guidance information by inputting the optical image and the target part information into the machine learning model.

In one embodiment, the machine learning model may be obtained through a training method including obtaining sample training data, the sample training data including historical optical images of historical target objects, and historical medical images of one or more target parts on the historical target objects; determining label information of the historical optical images based on fusion result information of the historical optical images and the historical medical images; and training an initial machine learning model using the historical optical images and the historical medical images as input data and the label information as output data or reference standards.

In one embodiment, the medical image may include the location of the lesion on the target part.

The determining the operation guidance information based on the optical image and the medical image may include determining the operation guidance information based on location information of the location of the lesion in the optical image and the medical image, the operation guidance information being capable of reflecting the location of the lesion relative to the target object.

In one embodiment, the medical image may further include depth information of the location of the lesion on the target part; the determining the operation guidance information associated with the target partn based on the optical image and the target part information may further include determining orientation information of the location of the lesion relative to an operation location and/or spatial location information of the location of the lesion relative to the target object based on the medical image and the optical image.

In one embodiment, the method may further include determining the indication information capable of being reflected on the surface of the target object based on the orientation information and/or the spatial location information and the operation guidance information.

In one embodiment, the obtaining target part information under a skin of the target object in a medical task may include obtaining a medical image of a target part under the skin of the target object.

The determining the operation guidance information associated with the target part based on the optical image and the target part information may further include determining an internal visualization image by performing an image fusion processing on the optical image and the medical image based on a second preset algorithm.

In one embodiment, the determining the operation guidance information associated with the target part based on the optical image and the target part information may further include marking operation location information in the internal visualization image.

In one embodiment, the second preset algorithm may include a first machine learning model, and the determining an internal visualization image by performing an image fusion processing on the optical image and the medical image based on a second preset algorithm may include inputting the optical image and the medical image into the first machine learning model, an output of the first machine learning model including the internal visualization image.

In one embodiment, the first machine learning model may be obtained through a training method including obtaining sample training data, the sample training data including historical optical images of historical target objects, and historical medical images of one or more target parts on the historical target objects; determining historical visualization images by performing the image fusion processing on the historical optical images and the historical medical images; and training an initial machine learning model using the historical optical images and the historical medical images as input data and the historical visualization images as output data.

In one embodiment, the second preset algorithm may further include a second machine learning model, and the determining the operation guidance information associated with the target part based on the optical image and the target part information may further include inputting the internal visualization image into the second machine learning model, an output of the second machine learning model including the operation location information.

In one embodiment, the second machine learning model may be obtained through a training method including obtaining sample training data, the sample training data including historical optical images of historical target objects, and historical medical images of one or more target parts on the historical target objects; determining historical visualization images by performing the image fusion processing on the historical optical images and the historical medical images; determining label information by marking historical operation location information on the historical visualization images; and training an initial machine learning model using the historical visualization images as input data and the label information as output data.

In one embodiment, the method may further include obtaining clinical information of the target object.

The determining the operation guidance information associated with the target part based on the optical image and the target part information may further include determining the operation guidance information based on the optical image, the target part information, and the clinical information.

In one embodiment, the target part information may include a medical image.

The determining the operation guidance information associated with the target part based on the optical image and the target part information may further include determining an internal visualization image by processing the optical image and the medical image based on a first machine learning model; and determining operation location information by processing the internal visualization image and the clinical information based on a second machine learning model.

In one embodiment, the method may further include obtaining real-time ultrasonic images of a surgical instrument acting on the target object; and determining an action path of the surgical instrument based on the real-time ultrasonic images, and displaying the action path.

In one embodiment, the determining an action path of the surgical instrument based on the real-time ultrasonic images, and displaying the action path may include obtaining real-time fused images by fusing the real-time ultrasonic image with the X-ray image of the target object; and displaying the action path in the real-time fused images.

In one embodiment, the method may further include obtaining a matching result by matching the action path with the planned path; and adjusting the action path based on the matching result.

In one embodiment, the method may further include obtaining X-ray images reflecting a final implantation location of the surgical instrument in the target object by adjusting a photographing angle of an image collection device.

In one embodiment, the obtaining an X-ray image of the target object may include obtaining X-ray images of the target object not implanted with surgical instrument from at least two photographing angles; and determining the X-ray image fused with the ultrasonic image of the target object not implanted with the surgical instrument based on clarities of the X-ray images obtained from the at least two photographing angles and locations of lesions displayed in the X-ray images obtained from the at least two photographing angles.

The present disclosure provides a method for determining operation guidance information. The method may include obtaining an optical image of a target object; obtaining target part information under a skin of the target object in a medical task; and determining operation guidance information associated with a target part based on the optical image and the target part information.

In one embodiment, the obtaining target part information under a skin of the target object in a medical task may include obtaining a medical image of the target part under the skin of the target object.

The determining the operation guidance information associated with a target part based on the optical image and the target part information may include determining the operation guidance information by processing the optical image and the medical image based on a first preset algorithm.

In one embodiment, the method may further include determining indication information capable of being reflected on a surface of the target object through an indication device based on the operation guidance information.

In one embodiment, the method may further include outputting the operation guidance information through a terminal device.

In one embodiment, the first preset algorithm may include a machine learning model, and the determining the operation guidance information associated with a target part based on the optical image and the target part information may further include determining the operation guidance information by inputting the optical image and the target part information into the machine learning model.

In one embodiment, the machine learning model may be obtained through a training method including obtaining sample training data, the sample training data including historical optical images of historical target objects, and historical medical images of one or more target parts on the historical target objects; determining label information of the historical optical images based on fusion result information of the historical optical images and the historical medical images; and training an initial machine learning model using the historical optical images and the historical medical images as input data and the label information as output data or reference standards.

In one embodiment, the medical image may include a location of a lesion on the target part.

The determining the operation guidance information based on the optical image and the medical image may include determining the operation guidance information based on location information of the location of the lesion in the optical image and the medical image, the operation guidance information being capable of reflecting the location of the lesion relative to the target object.

In one embodiment, the medical image may further include depth information of the location of the lesion on the target part; and the determining operation guidance information associated with a target part based on the optical image and the target part information may further include determining orientation information of the location of the lesion relative to an operation location and/or spatial location information of the location of the lesion relative to the target object based on the medical image and the optical image.

In one embodiment, the method may further include determining the indication information capable of being reflected on the surface of the target object based on the orientation information and/or the spatial location information and the operation guidance information.

In one embodiment, the obtaining target part information under a skin of the target object in a medical task may include obtaining a medical image of a target part under the skin of the target object.

The determining the operation guidance information associated with a target part based on the optical image and the target part information may further include determining an internal visualization image by performing an image fusion processing on the optical image and the medical image based on a second preset algorithm.

In one embodiment, the determining the operation guidance information associated with a target part based on the optical image and the target part information may further include marking operation location information in the internal visualization image.

In one embodiment, the second preset algorithm may include a first machine learning model, and the determining an internal visualization image by performing an image fusion processing on the optical image and the medical image may include inputting the optical image and the medical image into the first machine learning model, an output of the first machine learning model including the internal visualization image.

In one embodiment, the first machine learning model may be obtained through a training method including obtaining sample training data, the sample training data including historical optical images of historical target objects, and historical medical images of one or more target parts on the historical target objects; determining historical visualization images by performing an image fusion processing on the historical optical images and the historical medical images; and training an initial machine learning model using the historical optical images and the historical medical images as input data and the historical visualization images as output data.

In one embodiment, the second preset algorithm may further include a second machine learning model, and the determining operation guidance information associated with a target part based on the optical image and the target part information may further include inputting the internal visualization image into the second machine learning model, an output of the second machine learning model including the operation location information.

In one embodiment, the second machine learning model may be obtained through a training method including obtaining sample training data, the sample training data including historical optical images of historical target objects, and historical medical images of one or more target parts on the historical target objects; determining historical visualization images by performing an image fusion processing on the historical optical images and the historical medical images; determining label information by marking historical operation location information corresponding to the historical visualization images; and training an initial machine learning model using the historical visualization images as input data and the label information as output data.

In one embodiment, the method may further include obtaining clinical information of the target object. The determining operation guidance information associated with a target part based on the optical image and the target part information may include determining the operation guidance information based on the optical image, the target part information and the clinical information.

In one embodiment, the target part information may include a medical image.

The determining operation guidance information associated with a target part based on the optical image and the target part information may further include determining an internal visualization image by processing the optical image and the medical image based on a first machine learning model; and determining the operation location information by processing the internal visualization image and the clinical information based on a second machine learning model.

The present disclosure provides a detection device configured to obtain the X-ray image and the ultrasonic image of the method for path planning, and the method for determining the operation guidance information, comprising a housing and an X-ray detector accommodated in the housing, a detection surface of the X-ray detector being arranged opposite to the housing, wherein the detection device may further include an ultrasonic detector accommodated in the housing; the ultrasonic detector and the X-ray detector may move relatively; and the ultrasonic detector may move out of the detection surface of the X-ray detector.

In one embodiment, the detection surface of the X-ray detector may be arranged opposite to an inner surface of the housing; and the ultrasonic detector may be movably arranged in the housing, and the ultrasonic detector may also move on and be fit to the inner surface of the housing.

In one embodiment, the ultrasonic detector may be movably arranged inside the housing along a horizontal direction; and the X-ray detector may be movably arranged inside the housing along a vertical direction.

In one embodiment, a groove may be arranged on an inner surface of the ultrasonic detector close to the housing, and the groove may be used to accommodate an ultrasonic couplant.

In one embodiment, the ultrasonic couplant may be a solid couplant.

In one embodiment, the detection device may further include a scraping device, the scraping device may be slidably arranged on the inner surface of the housing, and the scraping device may be used to scrape off the ultrasonic couplant remaining on the inner surface.

In one embodiment, the detection device may further include a storage device, the storage device may be arranged on one side of the housing, and the storage device may be used to store the ultrasonic couplant scraped by the scraping device.

In one embodiment, the detection device may further include a first slide rail arranged along a horizontal direction, the first slide rail may be arranged on the housing, the first slide rail may be arranged between the inner surface of the housing and the X-ray detector, and the ultrasonic detector may be slidably arranged on the first slide rail.

In one embodiment, the detection device may further include a second slide rail vertically arranged on the housing, and the X-ray detector may be slidably arranged on the second slide rail.

In one embodiment, the detection device may be used for a mammography machine.

The present disclosure provides a multimodal medical imaging system. The multimodal medical imaging system may comprise a base. The detection device may be arranged on the base.

In one embodiment, the multimodal medical imaging system may be a mammography machine.

The present disclosure provides a device for path planning. The device for path planning may comprise an image obtaining module configured to obtain an X-ray image of a target object and mark a location of a lesion on the X-ray image of the target object; an image fusion module configured to obtain an ultrasonic image of the target object and obtain a fused image by fusing the ultrasonic image of the target object with the marked X-ray image; and a path planning module configured to obtain a planned path by performing path planning based on the location of the lesion in the fused image.

In one embodiment, the image obtaining module may be further configured to obtain operation guidance information associated with a target part, the target part including the location of the lesion; and the path planning module may be further configured to obtain a planned path by performing path planning based on the operation guidance information associated with the target part and the location of the lesion in the fused image.

In one embodiment, the device may further include an action path display module configured to obtain a real-time ultrasonic image of a surgical instrument acting on the target object; and determine an action path of the surgical instrument based on the real-time ultrasonic image, and display the action path.

The present disclosure provides a system for determining an operating location. The system for determining an operating location may comprise an optical image obtaining module configured to obtain an optical image of a target object; a target part obtaining module configured to obtain target part information under a skin of the target object in a medical task; and an operation guidance information determination module configured to determine operation guidance information associated with a target part based on the optical image and the target part information.

It can be seen from the above technical solutions that the present disclosure discloses methods for path planning, and methods, devices, and systems for determining operation guidance information. Specifically, an X-ray image of a target object may be obtained, and a location of a lesion may be marked on the X-ray image of the target object; an ultrasonic image of the target object may be also obtained, and a fused image may be obtained by fusing the ultrasonic image of the target object with the marked X-ray image. Further, a planned path may be obtained by performing the path planning based on a location of the lesion in the fused image. In this way, the problem that a single medical image provides relatively little information and cannot provide effective reference for surgery can be solved. The surgical instrument may be implanted based on the planned path, thereby improving the success rate of surgery and reducing surgical complications.

BRIEF DESCRIPTION OF THE DRAWINGS

In order to further clearly illustrate the technical solutions, in embodiments of the present disclosure or the prior art, a brief introduction of the drawings referred to the description of the embodiments or the prior art is provided below. Obviously, the drawings described below are only some examples or embodiments of the present disclosure. Those having ordinary skills in the art, without further creative efforts, may obtain other drawings according to the disclosed drawings.

DESCRIPTIONS OF THE DRAWING SIGNS

Figure 1:
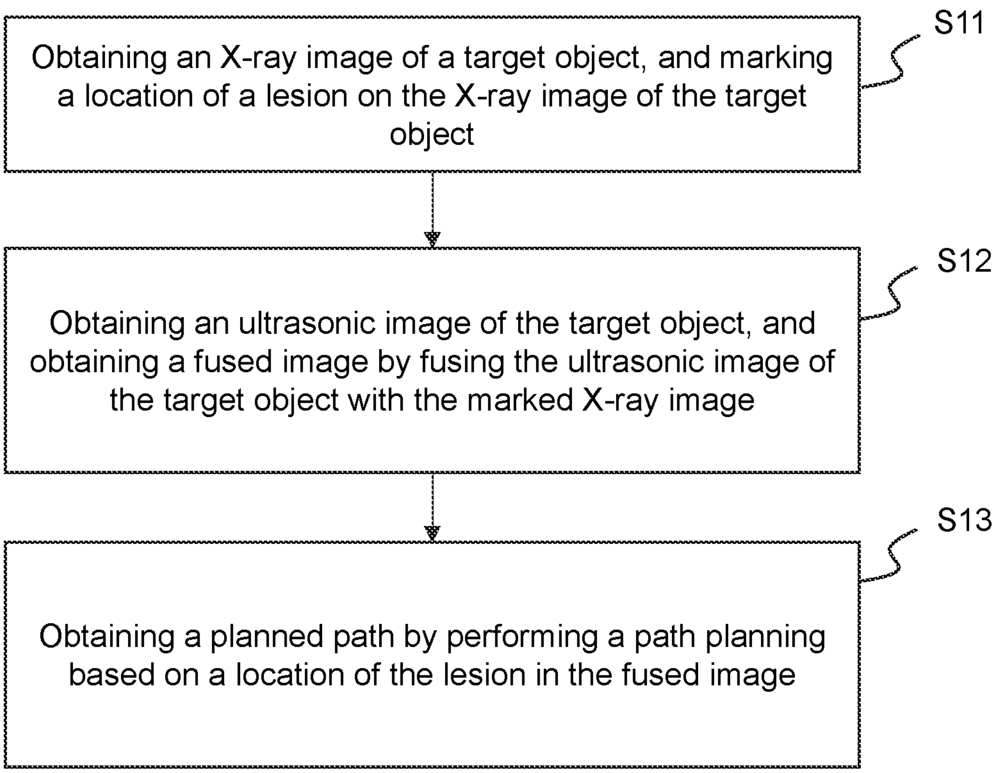
FIG. 1 is a flowchart illustrating a method for path planning according to some embodiments of the present disclosure.

Detection device 10, housing 100, accommodation space 110, inner surface 120, X-ray detector 210, X-ray emission source 220, ultrasonic detector 300, groove 310, scraping device 320, storage device 330, first slide rail 410, slideway 411, second slide rail 412, multimodal medical imaging system 20, base 510, support frame 520, mounting space 530, and tissue to be detected 540.

DETAILED DESCRIPTION

The following will clearly and completely describe technical solutions in embodiments of the present disclosure with reference to drawings in the embodiments of the present disclosure. Obviously, the described embodiments are only part of the embodiments of the present disclosure, not all of them. Based on the embodiments of the present disclosure, all other embodiments obtained by those having ordinary skills in the art without making creative efforts belong to the scope of protection of the present disclosure.

In order to more clearly illustrate the technical solutions of the embodiments of the present disclosure, the following briefly introduces the drawings that need to be used in the description of the embodiments. Obviously, the accompanying drawings in the following description are only some examples or embodiments of the present disclosure, and those having ordinary skills in the art, without creative efforts, may apply the present disclosure to other similar scenarios according to the drawings. Unless obviously obtained from the context or the context illustrates otherwise, the same numeral in the drawings refers to the same structure or operation.

It should be understood that “system”, “device”, “unit” and/or “module” as used herein is a method for distinguishing different components, elements, parts, portions or assemblies of different levels. However, the words may be replaced by other expressions if other words can achieve the same purpose.

As used in the present disclosure and the appended claims, the singular forms “a,” “an,” and “the” include plural referents unless the content clearly dictates otherwise. Generally speaking, the terms “comprising” and “including” only suggest the inclusion of clearly identified steps and elements, and these steps and elements do not constitute an exclusive list, and the method or device may also contain other steps or elements.

Although the present disclosure makes various references to certain modules or units in the system according to some embodiments of the present disclosure, any number of different modules or units may be used and run on the client and/or server. The modules are illustrative only, and different aspects of the systems and methods may use different modules.

The flowchart is used in the present disclosure to illustrate the operations performed by the system according to some embodiments of the present disclosure. It should be understood that the preceding or following operations are not necessarily performed in the exact order. Instead, various steps may be processed in reverse order or simultaneously. Meanwhile, other operations may be added to these procedures, or a certain step or steps may be removed from these procedures.

In the description of the present disclosure, it should be understood that the terms “center”, “longitudinal”, “transverse”, “length”, “width”, “thickness”, “upper”, “lower”, “front”, “back”, “left”, “right”, “vertical”, “horizontal”, “top”, “bottom”, “inner”, “outer”, “clockwise”, “counterclockwise”, “axial”, “radial”, “circumferential” and other indicated orientations or positional relationships are based on the orientations or positional relationships shown in the drawings, and are only for the convenience of describing the present disclosure and simplifying the description, rather than indicating or implying the referred device or elements must have certain orientations, be constructed and operated in certain orientations, and thus should not be construed as limiting the application.

In addition, the terms “first” and “second” are used for descriptive purposes only, and may not be interpreted as indicating or implying relative importance or implicitly specifying the quantity of indicated technical features. Accordingly, the features defined as “first” and “second” may explicitly or implicitly include at least one of these features. In the description of the present disclosure, “plurality” means at least two, such as two, three, etc., unless otherwise specifically defined.

In the present disclosure, unless otherwise clearly specified and limited, terms such as “installation”, “connection” and “fixation” should be interpreted in a broad sense, for example, it can be a fixed connection or a detachable connection, or integration; mechanical connection, or electrical connection; direct connection, or an indirect connection through an intermediary, or an internal communication between two elements or an interaction relationship between two elements, unless otherwise clearly defined. Those having ordinary skills in the art may understand the specific meanings of the above terms in the present disclosure according to specific situations.

In the present disclosure, unless otherwise clearly specified and limited, a first feature being “on” or “under” a second feature may mean that the first and second features are in direct contact, or that the first and second features are in indirect contact through an intermediary. Moreover, the first feature is “above” or “on” the second feature may mean that the first feature is directly above or obliquely above the second feature, or simply means that the first feature is higher in level than the second feature. The first feature “below” or “beneath” the second feature may mean that the first feature is directly below or obliquely below the second feature, or simply means that the first feature is lower in level than the second feature.

It should be noted that when an element is referred to as being “fixed on” or “disposed on” another element, it may be directly on another element or there may be an intervening element. When an element is referred to as being “connected to” another element, it may be directly connected to another element or there may be an intervening element. As used herein, the terms “vertical”, “horizontal”, "upper", "lower", "left", "right" and similar expressions are for the purpose of illustration only, and are not intended to represent the only embodiment.

FIG. 1 is a flowchart illustrating a method for path planning according to Embodiment 1 of the present disclosure. This embodiment may be applicable to the situation of path planning of surgical instrument implantation. The method may be performed by a device for path planning. The method may comprise the following operations.

S11. An X-ray image of a target object may be obtained, and a location of a lesion may be marked on the X-ray image of the target object.

A preoperative X-ray image of the target object may be photographed using a digital X-ray imaging device. Exemplarily, the preoperative X-ray image of the target object may be obtained using a C-arm X-ray machine, a mobile digital X-ray imaging device, or a suspended digital X-ray imaging device. Alternatively, the obtaining the X-ray image of the target object may include obtaining X-ray images of the target object not implanted with a surgical instrument from at least two photographing angles; and determining the X-ray image fused with an ultrasonic image of the target object not implanted with the surgical instrument based on clarities of the X-ray images obtained from the at least two photographing angles and locations of lesions displayed in the X-ray images obtained from the at least two photographing angles. The preoperative X-ray images of the target object obtained from the at least two angles may be obtained. A preoperative X-ray image whose clarity and displayed location of the satisfy needs of clinical diagnosis may be selected from the preoperative X-ray images, and a location of a lesion may be marked in the preoperative X-ray image. The marked preoperative X-ray image may be fused with a preoperative ultrasonic image of the target object.

S12. An ultrasonic image of the target object may be obtained, and a fused image may be obtained by fusing the ultrasonic image of the target object with the marked X-ray image.

The ultrasonic image may clearly display blood vessels and nerves of the target object. The preoperative ultrasonic image of the target object may be obtained by placing an ultrasonic detector on an affected part of the target object. A preoperative fused image may be obtained by fusing the marked preoperative X-ray image with the preoperative ultrasonic image of the target object. Alternatively, a method for image fusion may include a proximity display method, a direct fusion method, a feature selection fusion method, etc. An appropriate method may be selected for image fusion according to actual conditions.

S13. A planned path may be obtained by performing a path planning based on a location of the lesion in the fused image.

In the fused image of the preoperative X-ray image and the preoperative ultrasonic image, information such as the location of the lesion, blood vessels, and nerves may be displayed simultaneously. A reasonable path may be planned for a surgical instrument to act on the target object based on the information such as the location of the lesion, the blood vessels, and the nerves displayed in the preoperative fused image, to avoid other diseases caused by unnecessary damage to blood vessels and nerves during the action process of the surgical instrument, thereby providing a reference for the surgical instrument to act on the target object, and improving the accuracy and the success rate of surgical instrument implantation.

In one embodiment, the method for path planning may further include the following operations.

Operation guidance information associated with a target part may be obtained, and the target part may include the location of the lesion. The obtaining a planned path by performing a path planning based on a location of the lesion in the fused image may include obtaining the planned path by performing the path planning based on the operation guidance information associated with the target part and the location of the lesion in the fused image.

It should be noted that, the specific embodiment of obtaining operation location information of the target object may be found in the following embodiments relating to the method for determining the operation guidance information, which is not described herein.

In some embodiments of the present disclosure, the X-ray image of the target object may be obtained, and the location of the lesion may be marked on the X-ray image of the target object. The X-ray image may clearly display bone tissue information of the target object, which is helpful for marking the location of the lesion. The ultrasonic image may clearly display the blood vessels and nerves of the target object. The ultrasonic image of the target object may be obtained. The fused image may be obtained by fusing the ultrasonic image of the target object with the marked X-ray image. The planned path may be obtained by performing the path planning based on the location of the lesion in the fused image, which provides more reference information for surgical operations, and solves the problem that a single medical image provides relatively little information and cannot provide effective reference for surgery. The surgical instruments may be implanted based on the planned path, which can improve the success rate of surgery and reduce the surgical complications.

Figure 2:
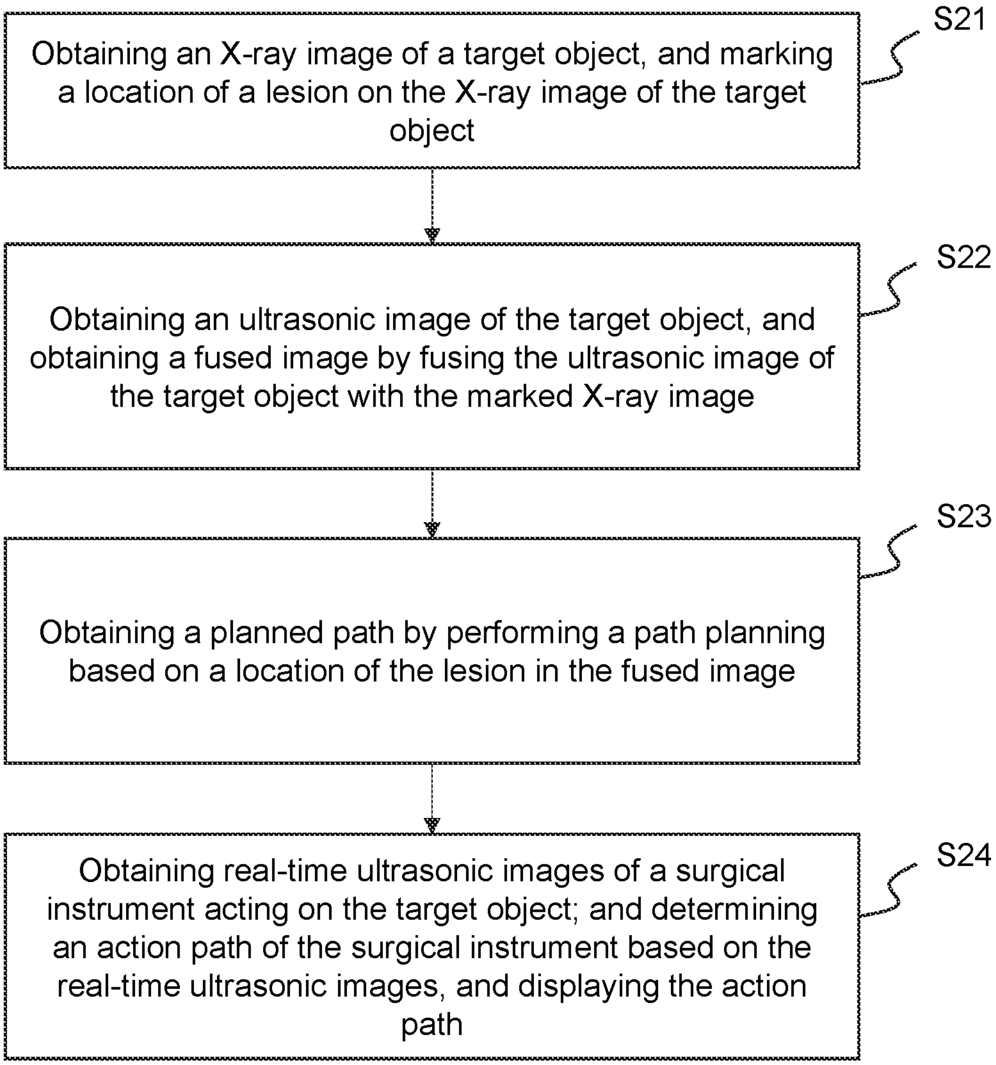
FIG. 2 is a flowchart illustrating a method for path planning according to some embodiments of the present disclosure.

FIG. 2 is a flowchart illustrating a method for path planning according to some embodiments of the present disclosure. This embodiment is further optimized based on the Embodiment 1. Alternatively, the method for path planning may further include obtaining a real-time ultrasonic image of a surgical instrument acting on the target object; determining an action path of the surgical instrument based on the real-time ultrasonic image; and displaying the action path, which may correct the deviation of the implantation of the surgical instrument, provide a reference for subsequent implantation, and improve the accuracy of the surgical instrument implanted into the lesion.

As shown in FIG. 2, the method may include the following operations.

S21. An X-ray image of a target object may be obtained, and a location of a lesion may be marked on the X-ray image of the target object.

S22. An ultrasonic image of the target object may be obtained, and a fused image may be obtained by fusing the ultrasonic image of the target object with the marked X-ray image.

S23. A planned path may be obtained by performing a path planning based on a location of the lesion in the fused image.

S24. Real-time ultrasonic images of a surgical instrument acting on the target object may be obtained; and an action path of the surgical instrument may be determined based on the real-time ultrasonic images, and the action path may be displayed.

During the operation, an ultrasonic detector may move with the movement of the surgical instrument to obtain intraoperative ultrasonic images in real time, and the real-time action of the surgical instrument may be displayed in the intraoperative ultrasonic images. Alternatively, the determining the action path of the surgical instrument based on the real-time ultrasonic images, and displaying the action path may include: obtaining real-time fused images by fusing the real-time ultrasonic images with the X-ray image of the target object; and displaying the action path in the real-time fused images. An intraoperative fused image may be obtained by fusing an intraoperative ultrasonic image obtained in real time with the marked preoperative X-ray image. The intraoperative fused image may display an implantation location of the current surgical instrument in the target object, and a location of the current surgical instrument relative to the lesion. The action path of the surgical instrument may be determined in real time based on the intraoperative ultrasonic images, and the action path may be displayed, and the action path may be compared with the planned path of the surgical instrument acting on the target object planned through the preoperative fused image, which can correct deviation of the action path of the surgical instrument, to make the surgical instrument be accurately implanted in the location of the lesion.

According to the above embodiments, the method for path planning may further include obtaining a matching result by matching the action path with the planned path; and adjusting the action path based on the matching result. The real-time action path of the surgical instrument may be matched with the planned path. If the action path of the surgical instrument is consistent with the planned path, it may mean that the action path of the implanted part of the surgical instrument is accurate, and subsequent implantation can be continued. When there is a deviation between the action path of the surgical instrument and the planned path, the action path of the surgical instrument may be adjusted in time to keep the action path consistent with the planned path, avoiding the wrong implantation location of the surgical instrument, and improving the success rate of the surgery.

In some embodiments of the present disclosure, the X-ray image of the target object may be obtained, and the location of the lesion may be marked on the X-ray image of the target object. The X-ray image may clearly display the bone tissue information of the target object, which is helpful for marking the location of the lesion. The ultrasonic image may clearly display the blood vessels and nerves of the target object. The ultrasonic image of the target object may be obtained, and the fused image may be obtained by fusing the ultrasonic image of the target object with the marked X-ray image. The planned path may be obtained by performing the path planning based on the location of the lesion in the fused image, which provides more reference information for surgical operations. The real-time ultrasonic images of the surgical instrument acting on the target object may be obtained, the action path of the surgical instrument may be determined based on the real-time ultrasonic images, and the action path may be displayed, which can correct the deviation of the implantation of the surgical instrument, provide a reference for subsequent implantation, improve the accuracy of the surgical instrument implanted into the lesion, and solve the problem that a single medical image provides relatively little information and cannot provide effective reference for surgery. The surgical instrument may be implanted based on the planned path, thereby improving the success rate of surgery and reducing surgical complications.

Figure 3:
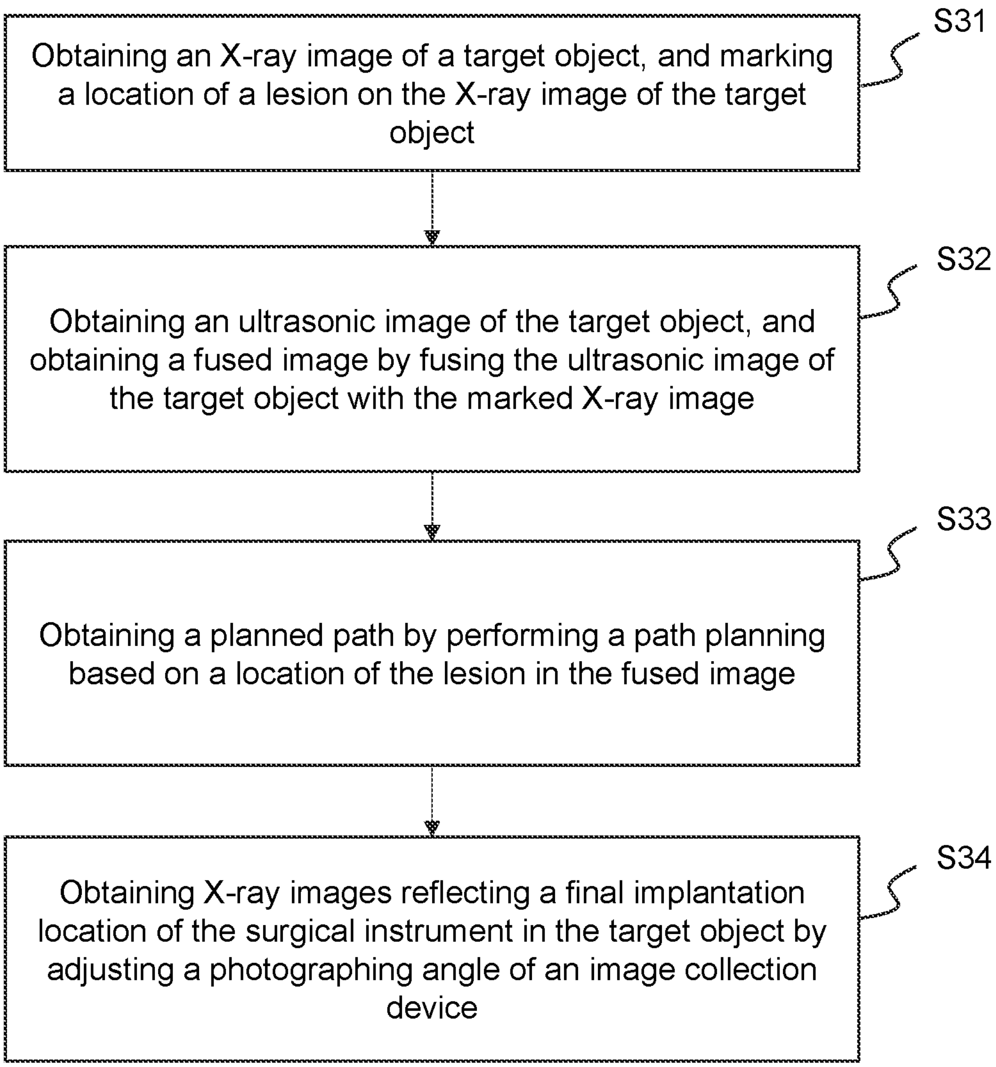
FIG. 3 is a flowchart illustrating a method for path planning according to some embodiments of the present disclosure.

FIG. 3 is a flowchart illustrating a method for path planning according to some embodiments of the present disclosure. This embodiment may be further optimized on the basis of the above embodiments. Alternatively, the method for path planning may further include obtaining X-ray images reflecting a final implantation location of a surgical instrument in a target object by adjusting a photographing angle of an image collection device. The final implantation location of the surgical instrument may be determined, to ensure the accuracy of surgical instrument implantation.

As shown in FIG. 3, the method may specifically include the following operations.

S31. An X-ray image of a target object may be obtained, and a location of a lesion may be marked on the X-ray image of the target object.

S32. An ultrasonic image of the target object may be obtained, and a fused image may be obtained by fusing the ultrasonic image of the target object with the marked X-ray image.

S33. A planned path may be obtained by performing a path planning based on the location of the lesion in the fused image.

S34. X-ray images reflecting a final implantation location of the surgical instrument in the target object may be obtained by adjusting a photographing angle of an image collection device.

When the operation of the surgical instrument is completed and implanted into the location of the lesion, and X-ray images of the target object may be obtained again by adjusting a photographing angle of a digital X-ray imaging device. Whether the surgical instrument is accurately implanted into the location of the lesion when the operation of the surgical instrument is completed may be displayed through the X-ray images corresponding to different photographing angles. If the surgical instrument is not implanted into the location of the lesion, the implantation location of the surgical instrument may be adjusted in time, to ensure the accuracy of the surgical instrument implantation, and prevent damage to the target object due to the implantation deviation of the surgical instrument.

In some embodiments of the present disclosure, the X-ray image of the target object may be obtained, and the location of the lesion may be marked on the X-ray image of the target object. The X-ray image may clearly display the bone tissue information of the target object, which is helpful for marking the location of the lesion. The ultrasonic image may clearly display the blood vessels and nerves of the target object. The ultrasonic image of the target object may be obtained, and the fused image may be obtained by fusing the ultrasonic image of the target object with the marked X-ray image. The planned path may be obtained by performing the path planning based on the location of the lesion in the fused image, which provides more reference information for surgical operations. The X-ray images reflecting the final implantation location of the surgical instrument in the target object may be obtained by adjusting photographing angle of the image collection device, to confirm the final implantation location of the surgical instrument, thereby ensuring the accuracy of the implantation of the surgical instrument, and solving the problem that a single medical image provides relatively little information and cannot provide an effective reference for the operation. The surgical instruments may be implanted based on the planned path, thereby improving the success rate of surgery and reducing surgical complications.

One or more embodiments of the present disclosure relate to a system for determining operation guidance information such as the operation guidance information in surgery. The operation guidance information may assist a doctor to determine an operation location on a surface skin corresponding to a patient's lesion. The surgical operations include but are not limited to an orthopedic operation. Merely by way of example, the orthopedic operation may be illustrated. For example, in the orthopedic operation, the patient's lesion may be usually located on the bone. When a doctor performs surgical treatment on the patient, he or she may determine the operation location on the surface skin, and then enter a location of the lesion from the operation location to perform treatment on the lesion.

Usually, when the doctor performs the surgical operation, he or she needs to select a location of a scalpel to operate on the patient (i.e., a location of the operation on the patient) based on experience. This way may completely rely on the experience of the doctor, and the selected location of scalpel may vary from person to person, which is not objective and accurate. According one or more embodiments of the present disclosure, the system for determining the operation guidance information may determine the operation guidance information based on an optical image and a medical image of the patient, and then determine the operation location on the surface of patient's skin. The operation location determined by some embodiments of the present disclosure may accurately correspond to the location of the lesion without relying on the doctor's experience.

The system for determining the operation guidance information may also display the operation location or indicate the operation location, after the operation guidance information on the surface skin of the patient is determined, so that the doctor may quickly obtain specific information of the operation location. The system for determining the operation guidance information may also be used to determine operation guidance information of other experimental subjects. In some embodiments, the other experimental subjects may include other living animals, or non-living experimental models. The system for determining the operation guidance information may be integrated into a surgical operation platform to assist the doctor in performing surgical operations. It should be understood that the application scenarios of the system for determining the operation guidance information in the present disclosure are only some examples or embodiments of the present disclosure, and those having ordinary skills in the art, without creative efforts, may also apply the present disclosure to other similar scenarios according to the drawings.

Figure 4:
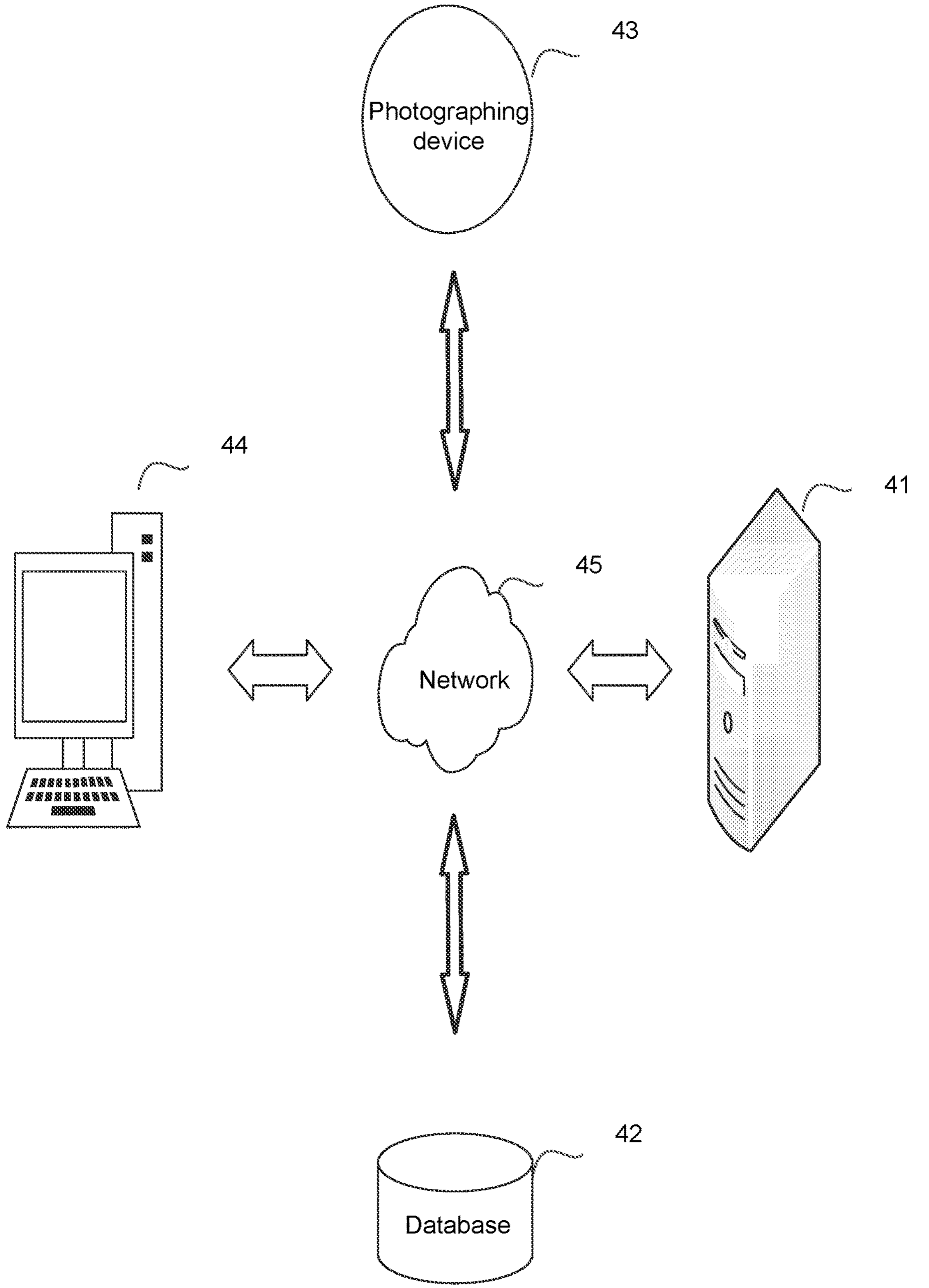
FIG. 4 is a schematic diagram illustrating an application scenario of a system for determining operation guidance information according to some embodiments of the present disclosure.

FIG. 4 is a schematic diagram illustrating an application scenario of a system for determining operation guidance information according to some embodiments of the present disclosure.

As shown in FIG. 4, the system 40 for determining the operation guidance information may include a server 41, a database 42, a photographing device 43, a terminal device 44, and a network 45.

In some embodiments, the server 41 may be configured to process information and/or data relating to determination of an operation location. For example, the server 41 may determine operation guidance information on a target object in an optical image based on a machine learning model. In some embodiments, the server 41 may also obtain information relating to the database 42 and/or the photography device 43 through the network 45. For example, the server 41 may obtain optical image information of the target object from the photographing device 43. As another example, the server 41 may obtain target part information of the target object in a medical task from the database 42.

In some embodiments, the server 41 may be an individual server or a server group. The server group may be centralized or distributed (e.g., the server 41 may be a distributed system). In some embodiments, the server 41 may be regional or remote. For example, the server 41 may access the information and/or materials stored in the database 42 and the photographing device 43 through the network 45. In some embodiments, the server 41 may be directly connected with the database 42 and the photographing device 43 to access the information and/or materials stored therein. In some embodiments, the server 41 may be executed on a cloud platform. For example, the cloud platform may include one of a private cloud, a public cloud, a hybrid cloud, or the like, or any combination thereof.

In some embodiments, the database 42 may be configured to store data relating to determining the operation guidance information. In some embodiments, the database 42 may store medical tasks and related information thereof. For example, the database 42 may store medical images in the medical tasks. As another example, the database 42 may store target part information of target objects in the medical tasks. In some embodiments, the database 42 may provide sample training data for training the machine learning model. In some embodiments, the database 42 may directly or indirectly communicate with the photographing device 43 and the server 41 through the network 45. Alternatively, the server 41 may access sample training data of the database 42 for training the machine learning model. In some embodiments, the sample training data may include historical optical images of historical target objects, and historical medical imaging images of one or more target parts on the historical target objects. In some embodiments, the database 42 or the server 41 or other external devices may calculate data labels of the sample training data. The database 42 may also include the data labels of the sample training data.

In some embodiments, the photographing device 43 may be a collection system for obtaining the optical image of the target object, and include but is not limited to at least one imaging device. In some embodiments, the photographing device 43 may be an optical imaging device, such as a camera or a video camera. In some embodiments, the photographing device 43 may communicate with the server 41 through the network 45, and store the obtained optical image information in the server 41 for subsequent processing. In some embodiments, the photographing device 43 may also communicate with the database 42, and store the obtained optical image information as the sample training data in the database 42 for training the machine learning model. In some embodiments, the photographing device 43 may also obtain real-time optical images of the target object. In some embodiments, the photographing device 43 may communicate with the terminal device 44 through the network 45, to display the obtained real-time optical images in the terminal device 44. For example, a camera component of the photographing device 43 may continuously obtain real-time image information during the doctor's operation, and display the real-time image information in the terminal device 44.

In some embodiments, the terminal device 44 may be configured to output the operation guidance information of the target object. In some embodiments, an output form of the operation guidance information may include but not limited to a display output or a voice output. Correspondingly, in some embodiments, the terminal device 44 may include a display device configured to display the operation guidance information of the target object. For example, the display device may mark specific location information of the operation guidance information with a striking mark (e.g., a red "X" mark) in the optical image of the target object. In some embodiments, the display device may also be configured to display an operation process in real time. For example, the display device may simultaneously display the doctor's current operation guidance information and a location of a mark, so that the doctor may accurately find the location of the mark for operation. In some embodiments, the terminal device 44 may include a voice output device, which outputs the specific information of the operation guidance information in a form of voice broadcast. In some embodiments, the terminal device 44 may further include an indication device configured to indicate the operation guidance information on the target object. For example, the indication device may include a laser indicator configured to project a laser beam to the target object. A location on the target object pointed by the laser beam may be the operation guidance information of the target object, and the doctor may operate the target object accordingly.

In some embodiments, the network 45 may facilitate the exchange of information and/or data. In some embodiments, one or more components of the system 40 (e.g., the server 41, the database 42, the photographing device 43, and the terminal device 44) for determining the operation guidance information may send the information and/or data to other components in the system 40 for determining the operation guidance information through the network 45. For example, the server 41 may obtain optical image information from the photographing device 43 through the network 45. As another example, the photographing device 43 may send the optical image to the terminal device 44 through the network 45. In some embodiments, the network 45 may be any form of wired or wireless network, or any combination thereof.

Figure 5:
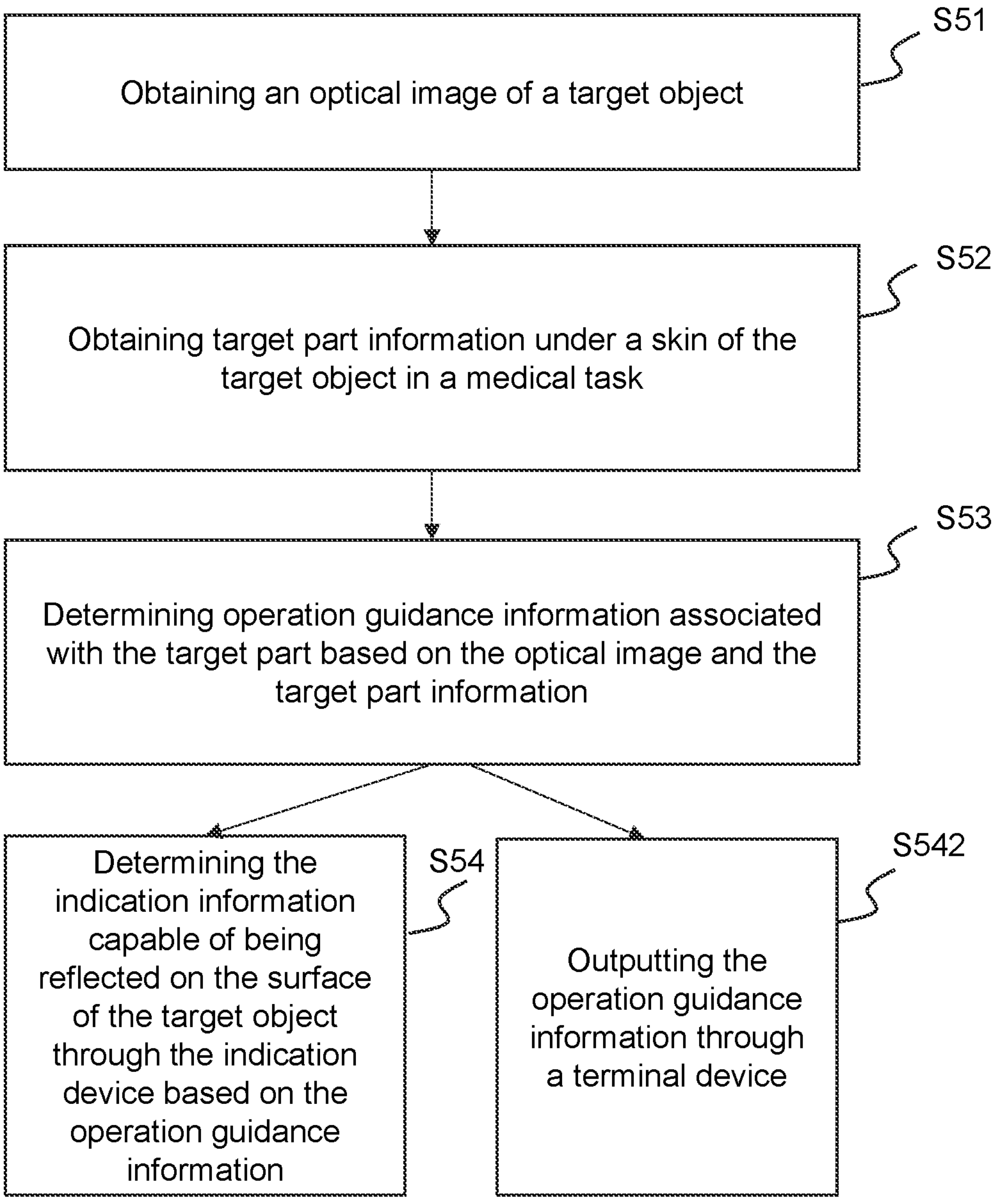
FIG. 5 is a flowchart illustrating an exemplary method for determining operation guidance information according to some embodiments of the present disclosure.

FIG. 5 is a flowchart illustrating an exemplary method for determining operation guidance information according to some embodiments of the present disclosure.

In 51, an optical image of a target object may be obtained. In some embodiments, step 51 may be performed by an optical image obtaining module 1110.

In some embodiments, the target object may be a living body, such as a human body, an animal body, or the like. In some embodiments, the target object may also be a non-living body, such as an experimental model. In some embodiments, the target object may be a patient in a medical relationship. In some embodiments, the optical image may be an image with continuously changing grayscale and color obtained by an optical photographing system. In some embodiments, the optical image may include surface information of the target object. In some embodiments, the optical image information may be information relating to the optical image of the target object, such as body part information of the optical image. In some embodiments, the photographing device 43 may include the optical photographing system. In some embodiments, the optical photographing system may include, but not limited to, a camera or a video camera that uses visible light imaging, infrared light imaging, or multi-band imaging. For example, the photographing device 43 may include a visible light camera capable of collecting visible light images of the target object. In some embodiments, the server 41 may obtain the collected optical image information from the photographing device 43 through the network 45. In some embodiments, the photographing device 43 may also send the collected optical image information to the terminal device 44 through the network, and the terminal device 44 may display the optical image information.

In 52, target part information under a skin of the target object in a medical task may be obtained. In some embodiments, step 52 may be performed by a target part obtaining module 1120.

In some embodiments, a target part may be understood as a part where related operations on the target object need to be performed in the medical task. In some embodiments, the part may be located under the skin of the target object. For example, the part may include a bone, a tissue, or an organ of a patient to be treated or operated on. In some embodiments, the target part information may be related information capable of reflecting the target part. For example, the target part information may be a name of the target part, or the like. In some embodiments, the medical task may be understood as a related medical operation performed on the target object. The medical operation may include but not limited to a surgical operation, an ultrasonography operation, a heart stent operation, a guide wire operation of angiography, or the like. In some embodiments, the server 41 may obtain the medical task of the target object. In some embodiments, the server 41 may also obtain medical protocol information relating to the medical task and a medical image of the target part. For example, the server 41 may obtain the medical image of the target part from a medical imaging device. In some embodiments, the medical protocol information may refer to information relating to a protocol of the medical task. In some embodiments, the medical image of the target part may refer to an image of the target part obtained by the medical imaging device. In some embodiments, the medical imaging device may include but not limited to an X-ray imaging device, a CT imaging device, a PET-CT device, a DSA device, an MRI imaging device, an ultrasonic imaging device, a nuclide imaging device, etc., or a multimodal device.

In some embodiments, the server 41 may obtain the target part information of the target object from the medical protocol information. For example, if the server 41 learns from the medical protocol information that the patient undergoes spinal displacement therapy, the server 41 may obtain the target part information of the target object including that the target part is the spine and the condition of the target part is spinal displacement. In some embodiments, the target part information of the target object may be determined from one or more images of the aforementioned medical imaging device. For example, an X-ray image may be obtained by the X-ray imaging device, and a doctor may determine a location of a lesion based on the X-ray image, such as a certain part of the spine. An MR image may be obtained by the MR imaging device, and the doctor may determine a location of a lesion based on the MR image, such as a certain part of the liver. A PET-CT image may be obtained by the PET-CT imaging device, and the doctor may determine a location of a lung lesion based on the PET-CT image. An angiographic fluoroscopy image may be obtained by the DSA device, and the doctor may determine a part where cardiac stenting or guide wire expansion is required.

In some embodiments, the server 41 may obtain the target part information of the target object from the medical image. For example, the server 41 may obtain the name of the target part, the location of the lesion of the target part, etc. from the medical image.

In 53, operation guidance information associated with the target part may be determined based on the optical image and the target part information. In some embodiments, step 53 may be performed by an operation guidance information determination module 1130.

In some embodiments, the server 41 may determine the operation guidance information associated with the target part on the target object based on the optical image and the target part information. In some embodiment, the operation guidance information may include information relating to one or more locations or one or more trajectories defined between a body surface and the target part in order to guide an operation element to the target part. The operation element may be a surgery element (e.g., a scalpel), an intrusive element (e.g., a guide wire or a stent), or an implantable element. In some embodiment, the operation guidance information may be visually displayed on the target object or on a display. When the operation guidance information is displayed on the display, the operation guidance information may be directly displayed on an image corresponding to the target object, or may be displayed on an image corresponding to a model. In some embodiment, the operation guidance information may include other non-visual information, such as voice, in addition to visual information. In some embodiment, the operation guidance information may include one or more location information. The location may be an operation location where the doctor performs the operation, also referred to as operation location information, which may reflect an orientation of the target part relative to the target object, to help the doctor to perform related operations on the target object based on the location. In some embodiments, the location may be a location where a doctor may operate a scalpel on the skin surface of the target subject during a surgical operation. In some embodiments, the location information may be understood as related information capable of reflecting the operation location.

In some embodiments, the operation guidance information may be reflected in the following operations. The operation guidance information may or may not be displayed in the optical image. In some embodiments, if the operation guidance information is displayed in the optical image, a contour diagram of the target part may be drawn on the surface of the target object based on the shape of the target part. The contour diagram may be the operation guidance information. Any location within the contour diagram may be the operation location. A location of the body surface corresponding to the target part may also be marked in the optical image (e.g., with "." or "x"). The location mark may be the operation guidance information, and the location corresponding to the location mark may be the operation location. For example, a location where a center point of the target part corresponds to the body surface may be marked as the operation guidance information. In some embodiments, the operation guidance information may also be displayed in the form of text in the optical image. For example, the operation guidance information may be displayed in the form of coordinates in the optical image. In some embodiments, the operation guidance information may also be described in the form of text display in the optical image. In some embodiments, if the operation guidance information is not displayed in the optical image, the operation guidance information may be displayed in the form of text. For example, coordinates of the operation location in the operation guidance information may be displayed on a display device. The operation guidance information may also be played in voice in the form of voice broadcast. For example, the coordinates of the operation location in the operation guidance information may be broadcast through a terminal device. As another example, description contents relating to the operation guidance information may be broadcast through a terminal device.

In some embodiments, the target part information may be obtained through medical protocol information, and the server 41 may determine the operation guidance information based on the optical image and the medical protocol information. In some embodiments, the target part information may be obtained through the medical image, and the server 41 may determine the operation guidance information by processing the optical image and the medical image based on a first preset algorithm. In some embodiments, the server 41 may display a specific orientation of the operation location by determining specific coordinates of the operation location in the optical image in the operation guidance information.

In some embodiments, according to the first preset algorithm, the operation guidance information on the target object may be determined based on the optical image and the target part information. In some embodiments, the first preset algorithm may include a machine learning model. In some embodiments, an input of the machine learning model may be the optical image of the target object and the medical image information of the target part, and an output of the machine learning model may be the operation guidance information on the target object. In some embodiments, the machine learning model may include, but not limited to, a convolutional neural network model, a recurrent neural network model, a full connect neural network model, or the like.

In some embodiments, the server 41 may determine the operation guidance information by inputting the optical image and the target part information into the machine learning model. In some embodiments, the server 41 may use the optical image and the medical image of the target object as input data and input the input data into the machine learning model, and the machine learning model may output the operation guidance information. In some embodiments, the machine learning model may directly output the optical image with a conspicuous mark. In some embodiments, the machine learning model may convert the input data into corresponding vector representation thereof. In some embodiments, the input data may be converted into an output vector after being calculated by the machine learning model. In some embodiments, the output vector of the machine learning model may be a vector representing the operation guidance information. In some embodiments, the server 41 may determine the specific information of the operation guidance information based on the output vector of the machine learning model including specific orientation information of the operation location. The specific training process of the machine learning model may be described in the related description of FIG. 3. In some embodiments, the server 41 may use the optical image, the medical image, and clinical information of the target object as input data and input the input data into the machine learning model, and the machine learning model may output the operation guidance information. In one example, the clinical information of a patient may include patient-specific information of the patient, such as historical surgical conditions, anatomical abnormalities, or vascular abnormalities, of the patient.

In some embodiments, the target part information may also include lesion location information on the target part. In some embodiments, the lesion location information may be understood as information capable of reflecting the situation of the location of the lesion, such as a size of the lesion, the location of the lesion, or the like. In some embodiments, the lesion location information may be embodied in protocol information of the medical task, i.e., the protocol information may include the orientation of the location of the lesion on the target part. In some embodiments, the lesion location information may be embodied in the medical image of the medical task. In some embodiments, the optimal operation location may be accurately located through the lesion location information, and the doctor may perform a surgical operation from the optimal operation location, to improve the treatment effect and efficiency. In some embodiments, the medical image of the target part may include the location of the lesion on the target part. In some embodiments, the server 41 may determine the operation guidance information based on the optical image and the location information of the lesion in the medical image. In some embodiments, the operation guidance information may reflect the location of the lesion relative to the target object. In some embodiments, the operation guidance information may include location information on the surface of the target object corresponding to the location of the lesion.

In some embodiments, the server 41 may output label information corresponding to the location of the lesion in the medical image through the machine learning model. In some embodiments, the label information may reflect the operation location on the surface of the target object.

In some embodiments, the medical image may further include depth information of the location of the lesion on the target part. In some embodiments, the depth information may be spatial location information capable of reflecting a depth of the location of the lesion in the target object. In some embodiments, the server 41 may determine the orientation information of the location of the lesion relative to the operation guidance information and/or the spatial location information of the location of the lesion relative to the target object based on the medical image and the optical image. In some embodiments, the orientation information may include the location information of the lesion relative to the operation location, and a direction of the lesion relative to the operation location. In some embodiments, the spatial location information may be location information of the lesion relative to the surface of the target object, which may include a surface location of the lesion corresponding to the target object and a depth location relative to the surface of the target object. In some embodiments, the doctor may select an accurate location, a direction, and a depth, of the operation to perform treatment on the lesion based on the orientation information and the spatial location information, helping the doctor to treat the lesion more accurately during the surgical operation.

In some embodiments, the server 41 may determine an internal visualization image by performing an image fusion processing on the optical image and the medical image based on a second preset algorithm. In some embodiments, the internal visualization image may refer to an image capable of visually displaying internal parts under the skin of the target object. In some embodiments, the internal visualization image may be used as the operation guidance information to provide operation guidance for the doctor. During the actual operation, the doctor may quickly and accurately select the location and direction of the operation based on the internal visualization image. In some embodiments, the second preset algorithm may include a first machine learning model, and the server 41 may determine the internal visualization image using the first machine learning model. In some embodiments, an input of the first machine learning model may include the optical image and the medical image, and an output of the first machine learning model may include the internal visualization image. In some embodiments, the first machine learning model may include but not limited to a convolutional neural network model, a recurrent neural network model, a full connect neural network model, or the like.

In some embodiments, the first machine learning model may be obtained through a training method including the following operations.

Historical optical images of historical target objects and historical medical images of one or more target parts on the historical target objects may be used as sample training data, and inputted into an initial machine learning model. In some embodiments, the sample training data may be obtained by the server 41.

Historical visualization images may be determined by performing the image fusion processing on the historical optical images and the historical medical images. In some embodiments, the historical visualization images may be internal visualization images of the historical target objects.

A trained first machine learning model may be obtained by training the initial machine learning model using the historical optical images and the historical medical images as input data, and the historical visualization images as output data.

In some embodiments, the server 41 may also mark the operation location information in the internal visualization image. In some embodiments, the operation location information may include information relating to the operation location indicated in the internal visualization image. In some embodiments, the information relating to the operation location may include, but not limited to, the operation location, an operation direction, an operation depth, an operation trajectory, or the location of the lesion. In some embodiments, the operation location information may be used as the operation guidance information to provide operation guidance for the doctor.

In some embodiments, the second preset algorithm may include a second machine learning model, and the server 41 may determine the operation location information using the second machine learning model. In some embodiments, an input of the second machine learning model may be the internal visualization image. In some embodiments, the input of the second machine learning model may also be the optical image and the medical image. In some embodiments, an output of the second machine learning model may include the operation location information.

In some embodiments, the second machine learning model may be obtained through a training method including the following operations.

Historical optical images of historical target objects and historical medical images of one or more target parts on the historical target objects may be used as sample training data, and inputted into an initial machine learning model. In some embodiments, the sample training data may be obtained by the server 41.

Historical visualization images may be determined by performing an image fusion processing on the historical optical images and the historical medical images. In some embodiments, the historical visualization images may be internal visualization images of the historical target objects.

Label information may be determined by marking historical operation location information corresponding to the historical visualization images. In some embodiments, the label information may be labels marked for information relating to historical operation locations in the historical visualization images, such as labels of historical operation locations, labels of historical operation trajectories, or the like.

A trained second machine learning model may be obtained by training the initial machine learning model using the historical visualization images as input data, and the label information as output data.

In some embodiments, the server 41 may obtain clinical information of the target object, and determine the operation guidance information based on the optical image, the target part information, and the clinical information. In some embodiments, the server 41 may determine the internal visualization image by inputting the optical image and the medical image into the first machine learning model for processing. In some embodiments, the server 41 may input the obtained internal visualization image and the clinical information into the second machine learning model, and determine the operation location information based on the second machine learning model. In some embodiments, the operation location information may be the operation guidance information associated with the target part determined by the server 41. In some embodiments, the server 41 may also implement the above process using a machine learning model (i.e., a third machine learning model). In some embodiments, an input of the third machine learning model may be the optical image, the medical image, and the clinical information, and an output of the third machine learning model may be the operation location information. In some embodiments, the third machine learning model may be obtained through a training method including the following operations. A trained third machine learning model may be obtained by training an initial machine learning model using historical optical images and historical clinical information of historical target objects, and historical medical images of one or more target parts on the historical target objects as sample training data, and historical operation location information of the historical target objects as labels.

After the operation guidance information is determined, the server 41 may send the operation information to different devices for output or display based on different application scenarios.

In some embodiments, the terminal device 44 may include an indication device. The server 41 may send the operation guidance information to the indication device for output. The indication device may send indication information to indicate the operation location in the operation guidance information on the surface of the target object. This method may help the doctor to intuitively see the specific orientation of the operation location on the surface of the target object, and the doctor may directly perform the operation based on the location indicated by the indication device. The subsequent steps of the embodiment may be further found in the related description of step 54.

In some embodiments, the server 41 may also send the operation guidance information to the terminal device 44, and the terminal device 44 may directly output the operation guidance information. The doctor may view or listen to the operation guidance information displayed or played on the terminal device 44, and quickly find the operation location on the surface of the target object, improving the accuracy and efficiency of the operation of the doctor. The subsequent steps of the embodiment may be found in the related description of step 542.

In 54, the indication information capable of being reflected on the surface of the target object through the indication device may be determined based on the operation guidance information. In some embodiments, step 54 may be performed by a first indication information determination module.

In some embodiments, the indication information may be information capable of indicating the operation guidance information. In some embodiments, the indication device may be a device capable of sending the indication information, such as a laser indicator. In some embodiments, the server 41 may determine the indication information based on the operation guidance information, and send the indication information to the indication device through the network 150. The indication device may indicate the operation guidance information on the surface of the target object based on the indication information. In this embodiment, the doctor may quickly find the location of the operation based on the location indicated by the indication device, and perform subsequent operations.

In some embodiments, the form of the indication information may include laser indication. In some embodiments, the indication device may be the laser indicator, and a laser beam emitted by the indication device may indicate the operation guidance information on the surface of the target object. For example, an operating table where the doctor performs a surgical operation may be provided with a laser indicator for indicating the operation guidance information. During the doctor's operation, the laser indicator may project a laser beam onto the target object, and the laser beam may leave a laser point on the surface of the target object, to indicate the operation location in the operation guidance information.

In some embodiments, the server 41 may also determine the indication information capable of being reflected on the surface of the target object based on the orientation information and/or the spatial location information and the operation guidance information. In some embodiments, the terminal device 44 may indicate the orientation information and/or the spatial location information through the indication device. For example, the indication device may indicate the operation location and the orientation information through the laser beam and the direction thereof, so that the doctor may determine the operation location and an operation direction. As another example, the indication device may indicate the operation location and the spatial location information on the target object, so that the doctor may determine the operation location and an operation depth. As another example, the indication device may simultaneously indicate the operation guidance information, the orientation information, and the spatial location information, so that the doctor may determine the operation location, the operation direction, and the operation depth. In some embodiments, there may be a plurality of indication devices respectively configured to indicate the orientation information and the spatial location information on the surface of the target object. In some embodiments, the indication device may also be an indication device capable of simultaneously indicating the orientation information and the spatial location information on the surface of the target object.

In 542, the operation guidance information may be outputted through a terminal device. In some embodiments, step 542 may be performed by an operation guidance information output module 1150.

In some embodiments, the server 41 may also send the operation guidance information to the terminal device 44 through the network 150, and the terminal device 44 may output the operation guidance information by way of display or voice broadcast.

In some embodiments, the terminal device 44 may include a display device. In some embodiments, the display device may display the optical image, and display an outline of the target part in the optical image, and use the outline as the output operation guidance information. In some embodiments, the display device may display the optical image, and use an conspicuous mark (e.g., a "x"-shaped mark or a "·"-shaped mark) in the optical image to mark the specific operation location of the operation guidance information in the optical image. In some embodiments, the display device may also describe the location information of the operation guidance information (e.g., the coordinates of the operation location) in the optical image using text. In some embodiments, the display device may not display the optical image, but directly display the location information of the operation guidance information (e.g., the coordinates of the operation location) through text information. When the doctor performs the operation, he or she may quickly find the location of the scalpel on the surface of the target object by viewing the operation guidance information displayed on the display device, thereby improving the accuracy and efficiency of the operation of the doctor.

In some embodiments, the terminal device 44 may also include a voice device, which may output the operation guidance information in the form of voice broadcast. For example, the voice device may broadcast a name of the part where the operation location is located in the human body, a distance value from other parts, etc. through voice. During the operation, the doctor may quickly find the location of the scalpel by listening to the voice broadcast information. In this way, the doctor does not need to perform other observation activities, which can effectively improve concentration of the doctor during the operation and improve the operation accuracy of the surgery.

In some embodiments, the system 100 for determining the operation guidance information may be integrated into a surgical operation platform to assist the doctor in performing surgical operations. The system 100 may collect the optical image of the patient during the operation, and indicate the operation guidance information for the patient's operation to the doctor. The doctor may perform the surgical operations on the patient based on the indication.

In some embodiments, the server 41 may also obtain scene information through the photographing device 130. In some embodiments, the scene information may include the location information of the target object in a scene. In some embodiments, the scene information may further include the location information of the indication device from the target object.

In some embodiments, the server 41 may also determine the indication information capable of being reflected on the surface of the target object based on the optical image, the target part information, the scene information, and a preset algorithm. The server 41 may determine the operation guidance information based on the optical image, the target part information, and the preset algorithm. The server 41 may also calculate the indication information indicating to the surface of the target object based on the operation guidance information and the scene information. For example, the server 41 may determine location coordinates of the indication device in the scene and a distance between the indication device and the target object through the scene information, and calculate and determine the indication information that the indication device indicates to the surface of the target object based on the coordinate information of the operation guidance information on the target object and the location coordinates of the indication device, and the distance between the indication device and the target object.

In some embodiments, the server 41 may also obtain indication information indicating to the surface of the target object based on a machine learning model. In some embodiments, the server 41 may input the optical image, the target part information, and the scene information into the machine learning model, and the machine learning model may directly output the indication information. In this embodiment, during the training process of the machine learning model, the scene information may be added to sample training data.

In some embodiments, the server 41 may send the indication information to the indication device, and the indication device may indicate the specific location information of the operation guidance information to the surface of the target object in the scene based on the indication information.

It should be noted that the above description about the process 200 is for example and description purposes only, and does not limit the scope of application of the present disclosure. Those skilled in the art may make various modifications and alterations to the process 200 under the teachings of the present disclosure. However, such modifications and alterations are still within the scope of the present disclosure.

In some embodiments, the server 41 may determine the operation guidance information by inputting the optical image and the target part information into the machine learning model. The training process of the machine learning model may be introduced hereinafter.

Figure 6:
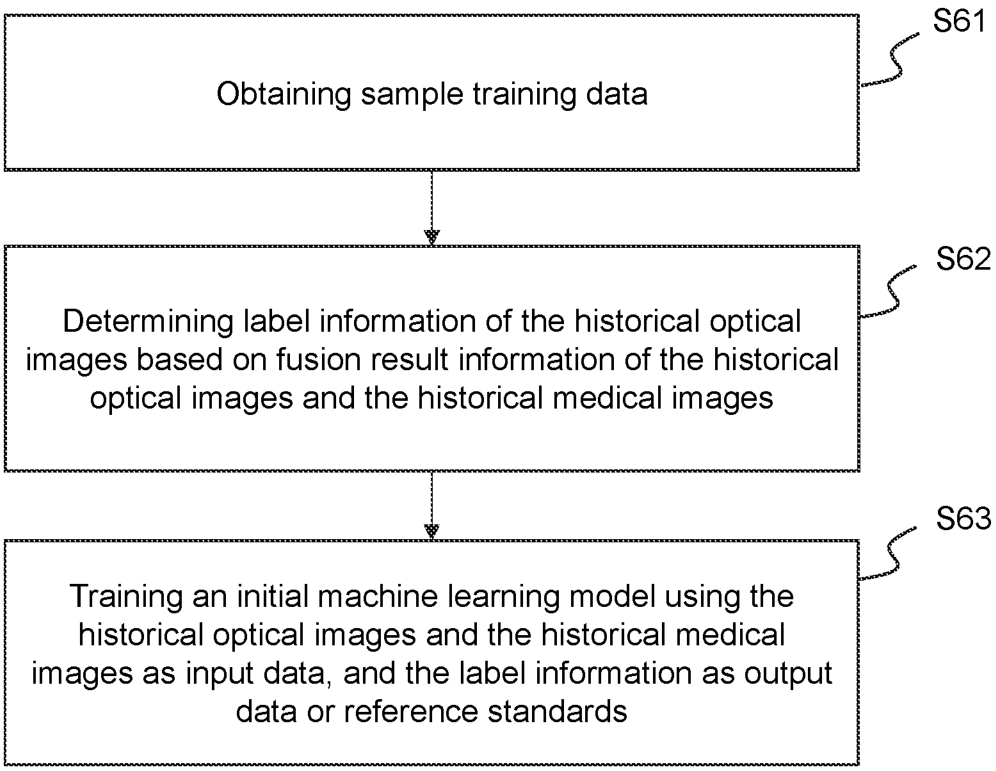
FIG. 6 is a flowchart illustrating an exemplary process for training a machine learning model according to some embodiments of the present disclosure.

FIG. 6 is flowchart illustrating an exemplary process for training a machine learning model according to some embodiments of the present disclosure. In some embodiments, the exemplary process of model training may be performed by a model training module.

In 61, sample training data may be obtained.

In some embodiments, the sample training data may include historical optical images of historical target objects, and historical medical images of one or more target parts on the historical target objects. In some embodiments, the historical target objects may be target objects in historical operations. The historical optical images may be optical images of the target objects collected during historical operations. The historical optical images may include surface information of the historical target objects.

The historical medical images may be medical images in medical tasks of the target objects in the historical operations. The historical medical images may include target part information of the historical target objects.

In 62, label information of the historical optical images may be determined based on fusion result information of the historical optical images and the historical medical images.

In some embodiments, after the sample training data is obtained, the sample training data may be processed. In some embodiments, the processing may include obtaining the fusion result information by fusing the historical optical images with the historical medical images. In some embodiments, the fusion result information may include the target part information of the historical target objects and surface information corresponding to the target parts. In some embodiments, the processing may further include determining the label information of the historical optical images based on the fusion result information. In some embodiments, the label information may be location information on the surfaces of the historical target objects.

In 63, an initial machine learning model may be trained using the historical optical images and the historical medical images as input data, and the label information as output data or reference standards.

In some embodiments, the initial machine learning model may be trained using the historical optical images and the historical medical images as the input data, and the label information as the output data or the reference standards. In some embodiments, the initial machine learning model may be a neural network model.

In some embodiments, after the input data pass through a neural network layers of the initial machine learning model, the initial machine learning model may output a result vector. The result vector may reflect the location information in the historical optical images. In some embodiments, after certain times of training, a similarity between an actual output result vector and a target vector representation in the above output data may become higher.

During the actual training process, it may be determined whether the training can be ended based on a comparison result between the actual output result vector and the target vector representation in the output data. In some embodiments, the similarity between the actual output result vector and the target vector representation in the output data may be determined by calculating a resemblance of the actual output result vector and the target vector representation. When the result vector and the output data are the same or similar, it may mean that the model is a trained machine learning model, and the training process may be terminated, to obtain the trained machine learning model.

In some embodiments, the training method of the machine learning model may further include the following operations.

Sample training data may be obtained, and the sample training data may include historical optical images of historical target objects.

Label information of the historical optical images may be determined by labelling the historical optical images of the historical target objects by an expert.

An initial machine learning model may be trained using the historical optical images as input data, and the label information as output data or reference standards.

The training methods in both embodiments may obtain the trained machine learning model. The training method of the latter embodiment may rely on the experience of experts, while the machine learning model obtained by the training method of the former embodiment may not rely on the experience of experts, and the obtained results may be more objective and accurate.

Figure 7:
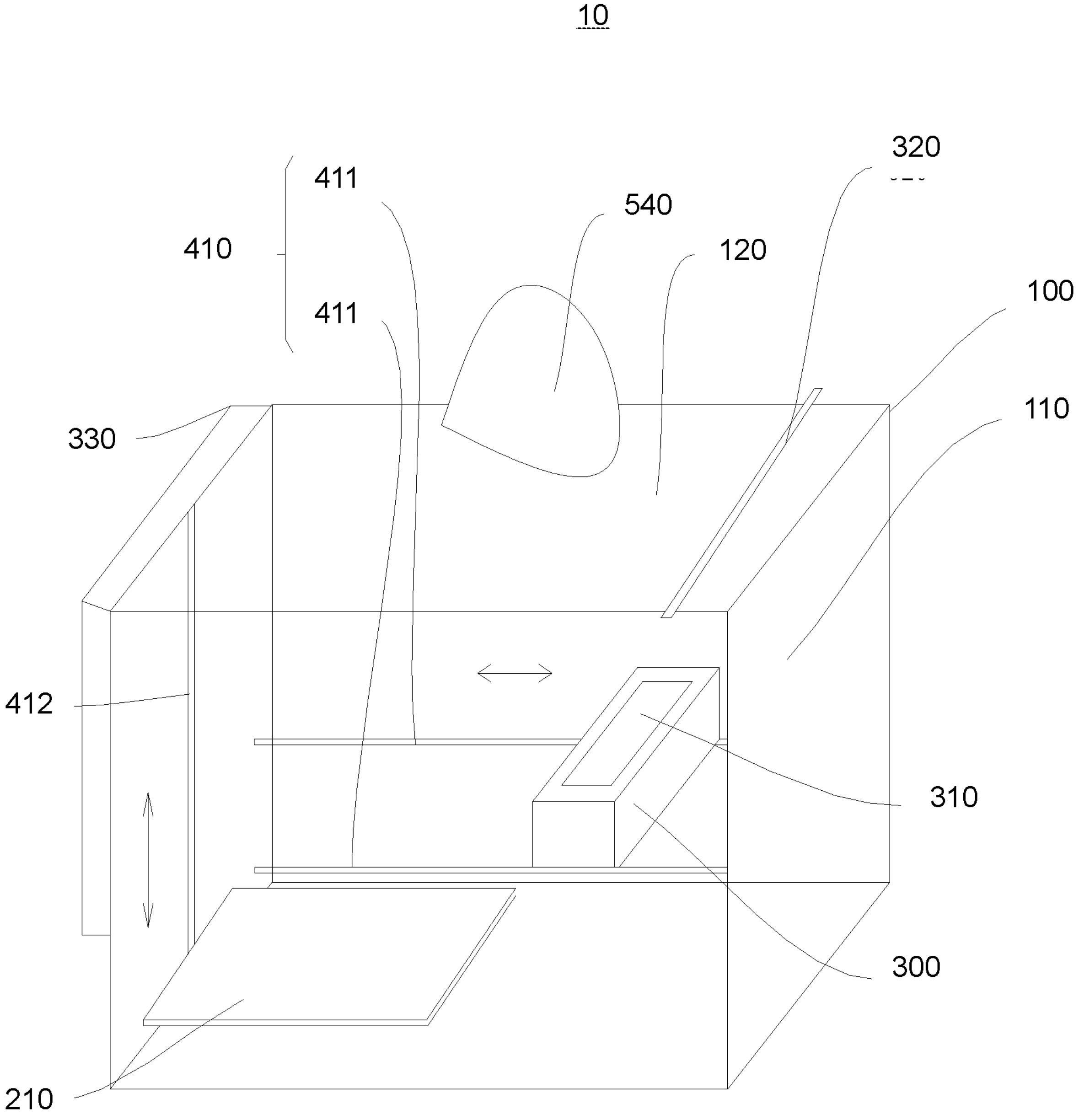
FIG. 7 is a three-dimensional structure diagram illustrating a detection device according to some embodiments of the present disclosure.

Referring to FIG. 7, FIG. 7 is a detection device 10 according to some embodiments of the present disclosure. The detection device 10 may be configured to obtain a X-ray image and an ultrasonic image. The detection device 10 may include a housing 100 and an X-ray detector 210 accommodated in the housing 100. A detection surface of the X-ray detector 210 may be arranged opposite to the housing 100. The detection device may further include an ultrasonic detector 300 accommodated in the housing 100. The ultrasonic detector 300 and the X-ray detector 210 may be capable of moving relatively. The ultrasonic detector 300 may move out of the detection surface of the X-ray detector 210.

The housing 100 may enclose to form an accommodation space 110. Both the X-ray detector 210 and the ultrasonic detector 300 may be disposed in the accommodation space 110. The shape of the housing 100 is not limited, as long as a space for accommodating the X-ray detector 210 and the ultrasonic detector 300 may be formed. A shape of the housing 100 may be set based on a location of the X-ray detector 210 and a location of the ultrasonic detector 300 in the housing 100. The housing 100 may be made of an alloy material or a polyester material.

The X-ray detector 210 may be a device for converting X-ray energy into an electrical signal for recording. The X-ray detector 210 may receive radiation, and then generate an electrical signal proportional to the radiation intensity. An intensity of the signal received by the X-ray detector 210 may depend on a tissue density in a section of a tissue to be detected 540. For example, the density of a bone may be relatively high, absorbing relatively many X-rays, and the signal received by the X-ray detector 210 may be relatively weak; a tissue with relatively low density, such as fat, may absorb relatively few X-rays, and the signal obtained by the X-ray detector 210 may be relatively strong. Therefore, the state of human tissue may be reflected based on the intensity of the signal received by the X-ray detector 210. The ultrasonic detector 300 may scan the human body with ultrasonic beams, and obtain an image of an internal organ by receiving and processing a reflected signal.

The X-ray detector 210 may be a flat panel detector. The detection surface of the X-ray detector 210 may be a region where the flat panel detector can realize a detection function within a range of its own plate. Structurally speaking, the detection surface may be a region where an electronic component with a photoelectric conversion function of the flat panel detector is located except for a frame of the flat panel detector.

The detection surface of the X-ray detector 210 may be arranged opposite to the housing 100, and thus the detection surface of the X-ray detector 210 may receive X-rays through the housing 100. The detection surface of the X-ray detector 210 may be arranged opposite to a top surface of the housing 100. The tissue to be detected 540 may be placed on a side where the top surface of the housing 100 is located.

The ultrasonic detector 300 and the X-ray detector 210 may be capable of moving relatively. That is, one of the ultrasonic detector 300 and the X-ray detector 210 may be fixed relative to the housing 100, while the other of the ultrasonic detector 300 and the X-ray detector 210 may be movably arranged relative to the housing 100. The ultrasonic detector 300 and the X-ray detector 210 may also be movably arranged relative to the housing 100.

It can be understood that both the ultrasonic detector 300 and the X-ray detector 210 may be connected with an inner wall of the housing 100, and location adjustment may be implemented by adjusting movements relative to the housing 100. The form of connecting the ultrasonic detector 300 and the X-ray detector 210 to the inner wall of the housing 100 may not be limited, as long as the functions of relative fixation and movement can be implemented.

An independent movement mechanism may also be arranged in the housing 100. The movement mechanism may be connected with both the ultrasonic detector 300 and the X-ray detector 210, to implement the function of controlling the ultrasonic detector 300 and the X-ray detector 210 to move independently or simultaneously. The movement mechanism may be a device such as a manipulator, a three-axis motion device, etc., to implement direct adjustment of the relative location of the ultrasonic detector 300 and the X-ray detector 210.

It can be understood that forms of the movement of the ultrasonic detector 300 and the X-ray detector 210 may adopt the technology in the prior art, and the present disclosure does not limit the specific type of movement structures, as long as the ultrasonic detector 300 and the X-ray detector 210 may achieve a specific movement range.

The ultrasonic detector 300 may move out of the detection surface of the X-ray detector 210, i.e., a projection of the ultrasonic detector 300 on a plane where the detection surface is located may not coincide with the detection surface. The ultrasonic detector 300 may not block the X-ray detector 210 from receiving X-rays.

The detection device 10 may include the housing 100 and the X-ray detector 210 accommodated in the housing 100. The detection surface of the X-ray detector 210 may be arranged opposite to the housing 100. Accordingly, the detection surface of the X-ray detector 210 may receive the X-rays incident from the housing 100. The detection device 10 may further include the ultrasonic detector 300 accommodated in the housing 100. The ultrasonic detector 300 and the X-ray detector 210 may move relatively. The ultrasonic detector 300 may move out of the detection surface of the X-ray detector 210.

When it is necessary to perform X-ray detection on the tissue to be detected 540, the ultrasonic detector 300 may move out of the detection surface of the X-ray detector 210, to make the ultrasonic detector 300 be away from the tissue to be detected 540 and the X-ray detector 210. That is, the ultrasonic detector 300 may not block the X-ray detector 210 from receiving X-rays. Then the ultrasonic detector 300 may not affect the work of the X-ray detector 210. When it is necessary to perform ultrasonic detection on the tissue to be detected 540, the ultrasonic detector 300 may be moved to a proper location to detect the tissue to be detected 540. As the X-ray detector 210 does not need to work at this time, the ultrasonic detector 300 may block the detection surface of the X-ray detector 210 and may emit ultrasonic waves to detect the tissue to be detected 540. The detection device 10 may select the X-ray detector 210 or the ultrasonic detector 300 to work based on needs, thereby fully utilizing the advantages of the X-ray detector 210 and the ultrasonic detector 300, and having the advantage of being flexible and convenient to use.

In one embodiment, the detection surface of the X-ray detector 210 may be arranged opposite to an inner surface 120 of the housing 100. The inner surface 120 may refer to a surface of an inner wall of the housing 100 opposite to the detection surface. The ultrasonic detector 300 may be movably arranged on the housing 100. The ultrasonic detector 300 may be also capable of moving on and be fitting to the inner surface 120 of the housing 100. The inner surface 120 of the housing 100 may be a panel surface at the top of the housing 100. That is, the X-rays may enter the detection surface of the X-ray detector 210 through the inner surface 120 of the housing 100. The ultrasonic detector 300 may move in the housing 100 as needed. The ultrasonic detector 300 may be fit to the inner wall, i.e., the inner surface 120, of the housing 100. When the tissue 540 to be detected is placed on the outer wall of the housing 100 opposite to the inner surface 120, the ultrasonic detector 300 may detect the tissue to be detected 540 through the inner surface 120 of the housing 100.

An outer wall opposite to the inner surface 120 of the housing 100 may be used to supporting the tissue to be detected. The panel surface where the inner surface 120 of the housing 100 is located may be used to place the tissue to be detected 540 directly or indirectly.

In one embodiment, the tissue to be detected may be breast tissue. The inner surface 120 of the housing 100 may be a surface of the housing 100, or may be a plate structure disposed on the housing 100. The X-ray detector 210 may be spaced apart from the panel surface where the inner surface 120 of the housing 100 is located. The X-ray detector 210 may be used to receive the X-rays. The X-rays may be emitted by an X-ray emission source 220. The X-ray emission source 220 may be disposed on a side of the inner surface 120 of the housing 100 away from the X-ray detector 210. That is, the X-rays emitted by the X-ray emission source 220 may be sent to the X-ray detector 210 through the inner surface 120 of the housing 100. When the tissue to be detected 540 is placed on the panel surface where the inner surface 120 of the housing 100 is located, the X-rays emitted by the X-ray emission source 220 may enter the X-ray detector 210 after passing through the tissue to be detected 540 and the inner surface of the housing 100 in sequence.

In one embodiment, the ultrasonic detector 300 may movably arranged inside the housing 100 along a horizontal direction. The X-ray detector 210 may be movably arranged in the accommodation space 110 along a vertical direction.

It can be understood that the inner surface 120 of the housing 100 and the X-ray detector 210 may be arranged at intervals. That is, there is a space between the inner surface 120 of the housing 100 and the X-ray detector 210. The inner surface 120 of the housing 100 and the X-ray detector 210 may be arranged relatively fixedly. A vertical distance between the inner surface 120 of the housing 100 and the X-ray detector 210 may also be adjusted as needs. The ultrasonic detector 300 may move on a horizontal plane between the inner surface 120 of the housing 100 and the X-ray detector 210. When it is necessary to perform X-ray detection on the tissue to be detected 540, the ultrasonic detector 300 may be moved on the horizontal plane between the inner surface 120 of the housing 100 and the X-ray detector 210, to make the ultrasonic detector 300 be away from the tissue to be detected 540 and the X-ray detector 210. That is, the ultrasonic detector 300 may not block the X-ray detector 210 from receiving the X-rays. At this time, the ultrasonic detector 300 may not affect the work of the X-ray detector 210. When it is necessary to perform ultrasonic detection on the tissue to be detected 540, the ultrasonic detector 300 may be moved to a location between the X-ray detector 210 and the inner surface 120 of the housing 100. As the X-ray detector 210 does not need to work at this time, the ultrasonic detector 300 may be moved above the X-ray detector 210, and may emit ultrasonic waves to detect the tissue to be detected 540.

In one embodiment, the detection surface of the ultrasonic detector 300 may be parallel to the inner surface 120 of the housing 100. A route of a planar movement of the ultrasonic detector 300 between the X-ray detector 210 and the inner surface 120 of the housing 100 may not be limited, as long as the ultrasonic detector 300 and the X-ray detector 210 may work separately without interfering with each other. Slideways 411 may be arranged on a plane between the X-ray detector 210 and the inner surface 120 of the housing 100. The ultrasonic detector 300 may slide on the slideways 411. The X-ray detector 210 may be movably arranged in the accommodation space 110 along the vertical direction. That is, when the inner surface 120 of the housing 100 is arranged horizontally, the X-ray detector 210 may be close to or away from the inner surface 120 of the housing 100 in the vertical direction.

When the X-ray detection is performed on the tissue to be detected 540, the X-ray detector 210 may move along the vertical direction, to make the X-ray detector 210 close to the inner surface 120 of the housing 100. The X-ray detector 210 may be close to the inner surface 120 of the housing 100, to improve the accuracy of receiving the X-rays. When the X-ray detector 210 is not required to work, the X-ray detector 210 may be away from the inner surface 120 of the housing 100. A large space may be formed between the inner surface 120 of the housing 100 and the X-ray detector 210. At this time, the ultrasonic detector 300 may be moved along the horizontal direction to a location between the X-ray detector 210 and the inner surface 120 of the housing 100. At this time, the tissue to be detected 540 placed on the inner surface 120 of the housing 100 may be detected by the ultrasonic detector 300. It can be understood that the accommodation space 110 may be provided with a slide rail arranged along the vertical direction. The X-ray detector 210 may be slidably disposed on the slide rail. A plurality of clamping structures may be arranged at intervals on the slide rail. The clamping structures may limit the location of the X-ray detector 210 on the slide rail, and may also limit a distance of the X-ray detector 210 relative to the inner surface 120 of the housing 100.

In one embodiment, the detection device 10 may further include a first slide rail 410 arranged along the horizontal direction. The first slide rail 410 may be arranged in the accommodation space 110. The first slide rail 410 may be arranged between the inner surface 120 of the housing 100 and the X-ray detector 210. The ultrasonic detector 300 may be slidably arranged on the first slide rail 410. The first slide rail 410 may include two slideways 411 arranged at intervals. The two slideways 411 may be respectively arranged on a plane parallel to the inner surface 120 of the housing 100. The ultrasonic detector 300 may cross the surfaces of the two slideways 411 and may slide on the surfaces of the slideways 411. It can be understood that the ultrasonic detector 300 may be connected with a motor. The motor may drive the ultrasonic detector 300 to move on the surfaces of the two slideways 411.

In one embodiment, the X-ray detector may be fixed relative to the accommodation space 110, and the ultrasonic detector 300 may slide horizontally on the first slide rail 410.

In one embodiment, the detecting device 10 may further include a second slide rail 412. The second slide rail 412 may be arranged along the vertical direction in the accommodation space 110. The X-ray detector 210 may be slidably arranged on the second slide rail 412. The second slide rail 412 may be one slideway, or two slideways arranged in parallel at intervals. The X-ray detector 210 may slide up and down along the second slide rail 412, to adjust a vertical distance between the X-ray detector 210 and the inner surface 120 of the housing 100.

In one embodiment, the ultrasonic detector 300 may be fit to a side of the inner surface 120 of the housing 100 located in the accommodation space 110. That is, the ultrasonic detector 300 may be fit to the inner wall of the inner surface 120 of the housing 100. That is, a probe of the ultrasonic detector 300 may be fit to a surface of the inner surface 120 of the housing 100 located in the accommodation space 110. The ultrasonic detector 300 may slide on the surface of the inner surface 120 of the housing 100 located in the accommodation space 110. Therefore, the ultrasonic detector 300 may be closer to the tissue to be detected 540, and the detection effect may be better. The ultrasonic detector 300 may be fit to the side of the inner surface 120 of the housing 100 located in the accommodation space 110. The inner surface 120 of the housing 100 may relatively define a horizontal plane for the movement of the ultrasonic detector 300, facilitating controlling the movement of the ultrasonic detector 300. Besides, the ultrasonic detector 300 may be fit to the side of the inner surface 120 of the housing 100 located in the accommodation space 110, which can further improve the compactness of the detection device 10 and reduce the space occupied by the detection device 10.

In one embodiment, a place of the ultrasonic detector 300 close to the inner surface 120 of the housing 100 may be provided with a groove 310. The groove 310 may be configured to accommodate an ultrasonic couplant. The shape of the groove 310 is not limited, as long as the groove 310 may be filled with the ultrasonic couplant. A cross section of the groove 310 may be rectangular, circular, elliptical or polygonal. The groove 310 may be sealed. For example, a sealing ring may be arranged at an opening of the groove 310, and then the opening of the groove 310 may be fit to the surface of the inner surface 120 of the housing 100, to achieve the effect of sealing the groove 310. In one embodiment, the groove 310 may also be sealed without air by vacuumizing the groove 310. It can be understood that during ultrasonic examination, the air between the probe of the ultrasonic detector 300 and the patient's skin may hinder the transmission of ultrasonic waves into the human body. In order to obtain a high-quality and clear image, the ultrasonic couplant may be used to connect the probe with the body surface of the patient. By sealing the groove 310, the air may be prevented from obstructing the transmission of ultrasonic waves into the human body, and the detection effect may be improved.

In one embodiment, the ultrasonic couplant may be a solid couplant. The shape of the solid couplant may be the same as that of the groove 310, so it is convenient to take and put the solid couplant from/in the groove 310. The solid couplant is not easy to blend into the air, thereby improving the detection effect. The solid couplant may also facilitate transportation. In one embodiment, the ultrasonic couplant may be made of konjac powder as a main raw material.

In one embodiment, the ultrasonic couplant may also be a liquid couplant. When the liquid couplant is used, a liquid seal structure may be arranged in the groove. The liquid couplant may be injected into the groove through a hydraulic system.

In one embodiment, the detection device 10 may further include a scraping device 320. The scraping device 320 may be slidably arranged on the inner surface 120 of the housing 100. The scraping device 320 may be configured to scrape the ultrasonic couplant left on the inner surface of the housing 100. When the ultrasonic detector 300 detects the tissue to be detected 540, usually the ultrasonic couplant may be required. After the tissue to be detected 540 leaves the inner surface 120 of the housing 100, the ultrasonic couplant remaining on the inner surface 120 may be scraped by the scraping device 320.

In one embodiment, the scraping device 320 may be arranged along a width direction of the inner surface 120 of the housing 100, and a surface of the scraping device 320 in contact with the inner surface 120 of the housing 100 may be a silicone material.

In one embodiment, the detection device 10 may further include a storage device 330. The storage device 330 may be arranged on one side of the housing 100. The storage device 330 may be configured to store the ultrasonic couplant scraped by the scraping device 320. The storage device 330 may be arranged on an edge of the housing 100. The storage device 330 may be a cubic structure with an opening, or a bag-like structure with an opening fixed to the edge of the housing 100. After the ultrasonic couplant remaining on the surface of the inner surface 120 of the housing 100 is scraped to the edge of the inner surface 120 of the housing 100 by the scraping device 320, the ultrasonic couplant may fall into the storage device 330. The ultrasonic couplant may be recovered through the storage device 330 to avoid waste.

In one embodiment, the detection device may be used for a mammography machine.

Figure 8:
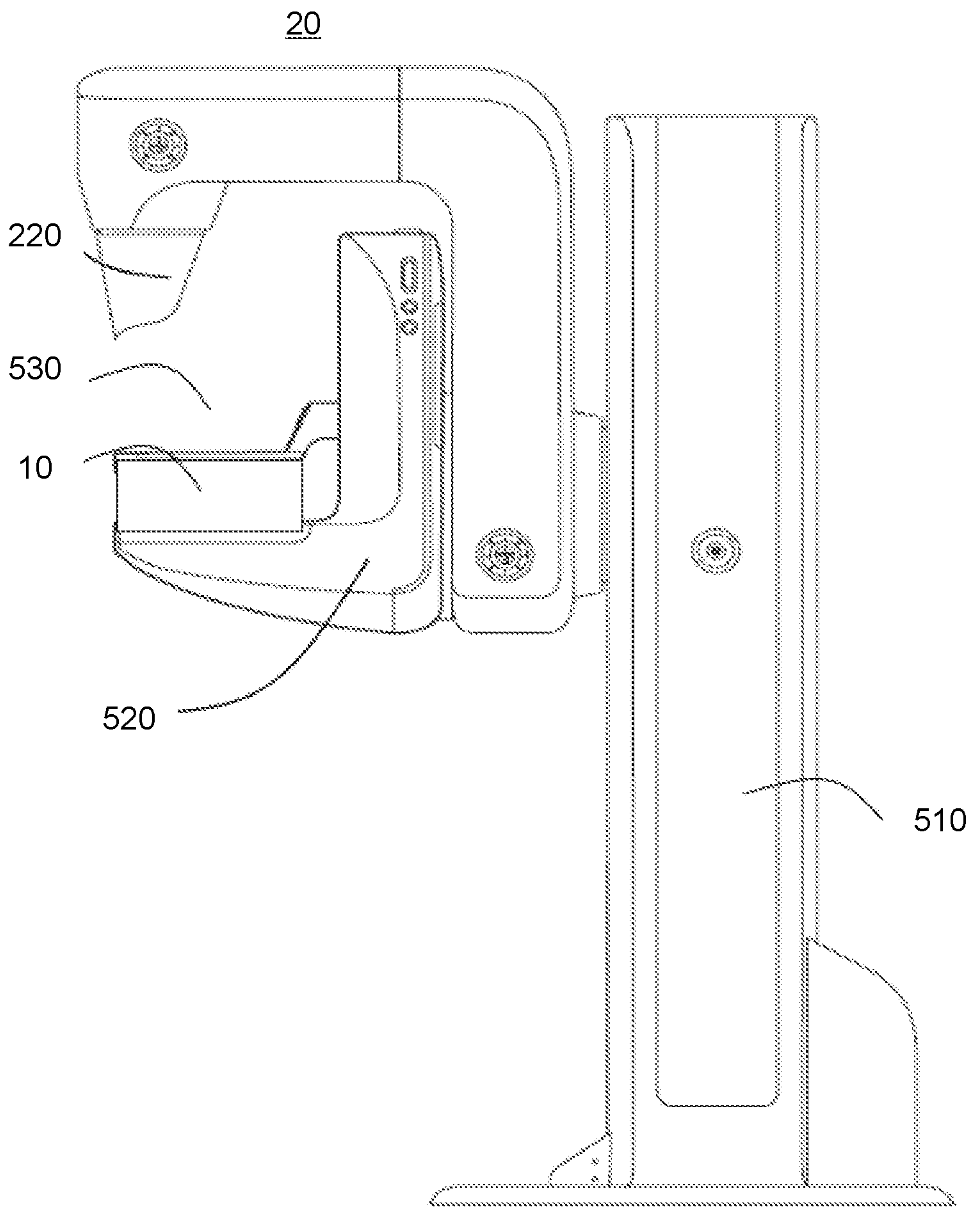
FIG. 8 is a side view illustrating a multimodal medical imaging system according to some embodiments of the present disclosure.
Figure 9:
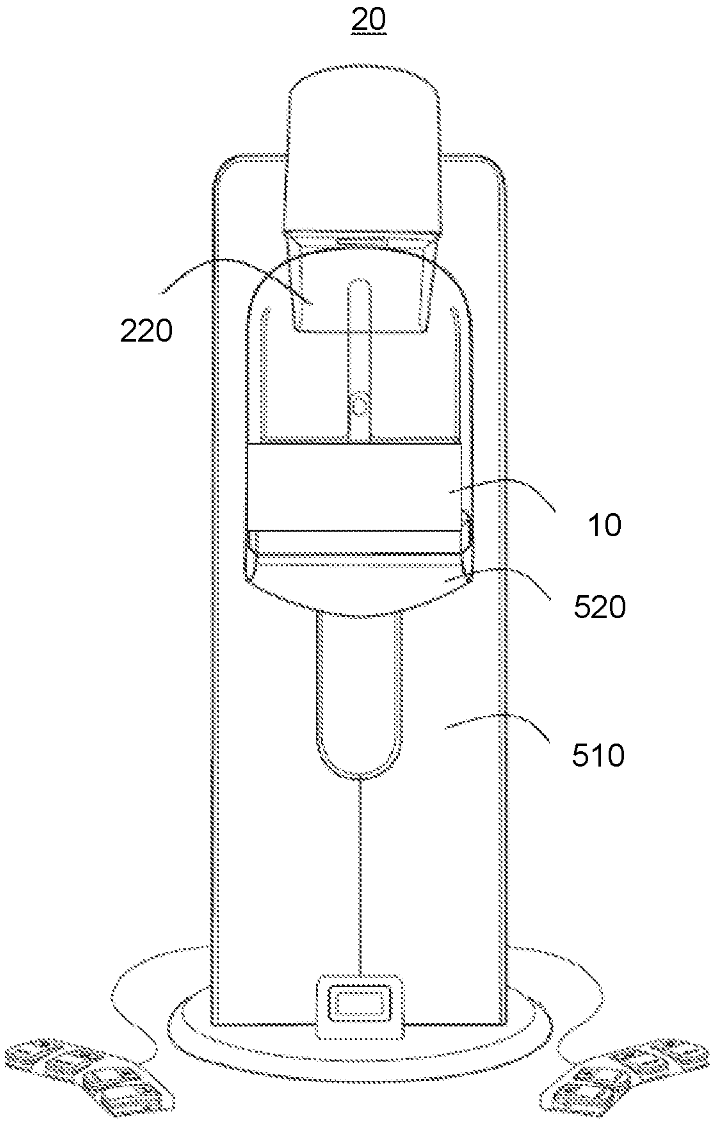
FIG. 9 is a front view illustrating a multimodal medical imaging system according to some embodiments of the present disclosure.

Referring to FIG. 8 and FIG. 9, some embodiments of the present disclosure further provide a multimodal medical imaging system 20. The multimodal medical imaging system 20 may include a base 510 and the detection device 10. The detection device 10 may be arranged on the base 510. The base 510 may also be provided with a support frame 520. A mounting space 530 for accommodating the housing 100 may be arranged in the support frame 520. The X-ray emission source 220 may be arranged on a top of the support frame 520. The tissue to be detected 540 may be placed between the X-ray emission source 220 and a panel where the inner surface 120 of the housing 100 is located. The X-rays emitted by the X-ray emission source 220 may be received by the X-ray detector 210 after passing through the tissue to be detected 540.

In one embodiment, the multimodal medical imaging system 20 may be a mammography machine.

The technical features of the above-mentioned embodiments may be combined arbitrarily. To make the description concise, not all possible combinations of the technical features in the above-mentioned embodiments are described. However, the combinations of the technical features, as long as no contradiction, should be considered as within the scope of the present disclosure.

Figure 10:
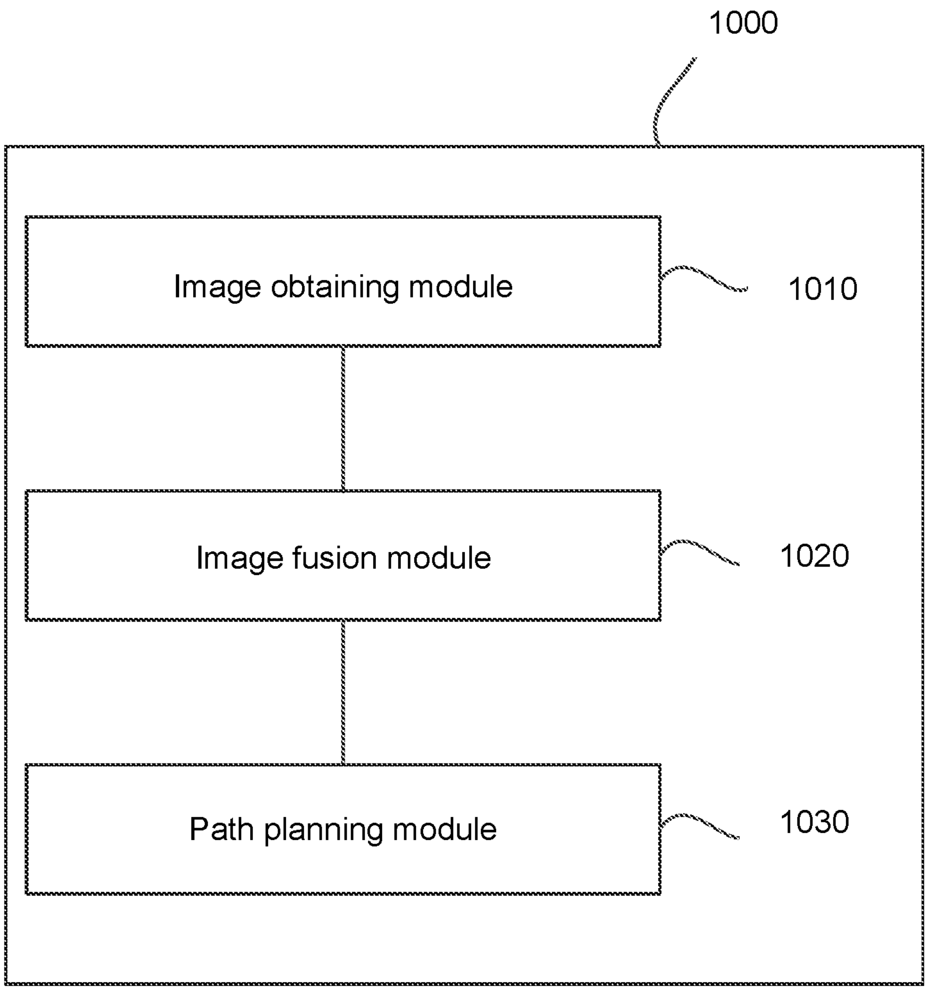
FIG. 10 is a structural diagram illustrating a device for path planning according to some embodiments of the present disclosure.

FIG. 10 is a structural diagram illustrating a device 1000 for path planning according to some embodiments of the present disclosure. The device for path planning may include an image obtaining module 1010, an image fusion module 1020, and a path planning module 1030.

The image obtaining module 1010 may be configured to obtain an X-ray image of a target object, and mark a location of a lesion on the X-ray image of the target object. The image fusion module 1020 may be configured to obtain an ultrasonic image of the target object, and obtain a fused image by fusing the ultrasonic image of the target object with the marked X-ray image. The path planning module 1030 may be configured to obtain a planned path by performing a path planning based on the location of the lesion in the fused image.

In the solution of the above embodiment, the image obtaining module 1010 may obtain operation guidance information associated with a target part, the target part including the location of the lesion.

The path planning module 1030 may be configured to obtain the planned path by performing the path planning based on the operation guidance information associated with the target part and the location of the lesion in the fused image.

It can be understood that when the image obtaining module 1010 is configured to obtain operation location information of the target object, the image obtaining module 1010 may be equivalent to a system for determining an operation location. The specific implementation method may refer to the following embodiments of the system for determining the operation location, which is not described herein.

In some embodiments, the path planning module 1030 is further configured to obtain the planned path by planning a path of a surgical instrument acting on the target object based on a preoperative fused image.

In some embodiments, the device for path planning may further include a real-time ultrasonic image obtaining module 1020.

The real-time ultrasonic image obtaining module 1020 is configured to obtain real-time ultrasonic images of the surgical instrument acting on the target object, determine an action path of the surgical instrument based on the real-time ultrasonic images, and display the action path.

In the above embodiments, the real-time ultrasonic image obtaining module 1020 may include an image fusion unit and a fused image display unit.

The image fusion unit is configured to obtain real-time fused images by fusing the real-time ultrasonic images with an X-ray image of the target object not implanted with the surgical instrument.

The fused image display unit is configured to display the action path in the real-time fused image.

In the above embodiments, the image obtaining module 1010 may include an X-ray image obtaining unit and an image determination unit.

The X-ray image obtaining unit is configured to obtain X-ray images of the target object not implanted with the surgical instrument from at least two photographing angles; and The image determination unit is configured to determine the X-ray image fused with the ultrasonic image of the target object not implanted with the surgical instrument based on clarities of the X-ray images obtained from the at least two photographing angles and locations of lesions displayed in the X-ray images obtained from the at least two photographing angles.

According to some embodiments of the present disclosure, the X-ray image of the target object may be obtained, and the location of the lesion may be marked on the X-ray image of the target object. The ultrasonic image of the target object may also be obtained, and the fused image may be obtained by fusing the ultrasonic image of the target object with the marked X-ray image. Further, he planned path may be obtained by performing the path planning based on the location of the lesion in the fused image. In this way, the problem that a single medical image provides relatively little information and cannot provide effective reference for surgery can be solved. The surgical instrument may be implanted based on the planned path, thereby improving the success rate of surgery and reducing surgical complications.

The device for path planning may perform the method for path planning provided in any embodiment of the present disclosure, and have functional modules and beneficial effects for performing the method.

Figure 11:
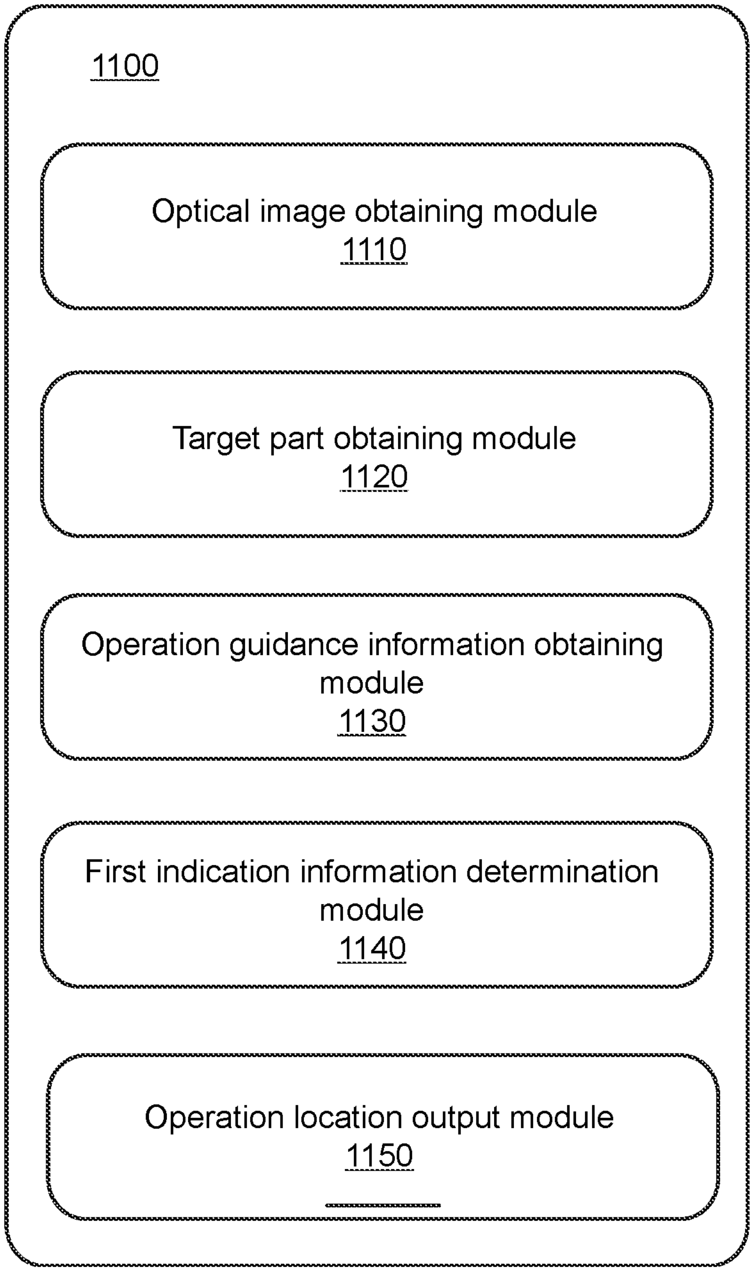
FIG. 11 is a block diagram illustrating a system for determining operation guidance information according to some embodiments of the present disclosure.

FIG. 11 is a block diagram illustrating a system 1100 for determining an operation location according to some embodiments of the present disclosure.

As shown in FIG. 11, the system 1100 for determining the operation location may include an optical image obtaining module 1110, a target part obtaining module 1120, an operation guidance information determination module 1130, a first indication information determination module 1140, and an operation guidance information output module 1150.

FIG. 11 is a block diagram illustrating a system for determining operation guidance information according to some embodiments of the present disclosure.

As shown in FIG. 11, the system 1100 for determining the operation guidance information may include an optical image obtaining module 1110, a target part obtaining module 1120, an operation guidance information determination module 1130, a first indication information determination module 1140, and an operation guidance information output module 1150.

In some embodiments, the optical image obtaining module 1110 may be configured to obtain an optical image of a target object.

In some embodiments, the target part obtaining module 1120 may be configured to obtain target part information of the target object in a medical task. In some embodiments, the target part obtaining module 1120 may be further configured to obtain a medical image of a target part under a skin of the target object.

In some embodiments, the operation guidance information determination module 1130 may be configured to determine the operation guidance information on the target object based on the optical image, the target part information, and a preset algorithm. In some embodiments, the operation guidance information determination module 1130 may be further configured to determine the operation guidance information by processing the optical image and the medical image based on the first preset algorithm. In some embodiments, the operation guidance information determination module 1130 may be further configured to determine the operation guidance information by inputting the optical image and the target part information into a machine learning model. In some embodiments, the operation guidance information determination module 1130 may be further configured to determine the operation guidance information based on location information of the location of the lesion in the optical image and the medical image. The operation guidance information may reflect a location of the lesion relative to the target object. In some embodiments, the operation guidance information determination module 1130 may be further configured to determine orientation information of the location of the lesion relative to the operation guidance information and/or spatial location information of the location of the lesion relative to the target object based on the medical image and the optical image. In some embodiments, the operation guidance information determination module 1130 may be further configured to determine an internal visualization image by performing an image fusion processing on the optical image and the medical image based on a second preset algorithm. In some embodiments, the operation guidance information determination module 1130 may be further configured to mark the operation location information in the internal visualization image. In some embodiments, the operation guidance information determination module 1130 may be further configured to input the optical image and the medical image into a first machine learning model. An output of the first machine learning model may include the internal visualization image. In some embodiments, the operation guidance information determination module 1130 may be further configured to input the internal visualization image into a second machine learning model. An output of the second machine learning model may include the operation location information. In some embodiments, the system 1100 for determining the operation guidance information may further include a clinical information obtaining module configured to obtain clinical information of the target object. The operation guidance information determination module 1130 may be further configured to determine the operation guidance information based on the optical image, the target part information, and the clinical information. In some embodiments, the operation guidance information determination module 1130 may be further configured to determine the internal visualization image by processing the optical image information and the medical image based on the first machine learning model; and determine the operation location information by processing the internal visualization image and the clinical information based on the second machine learning model.

In some embodiments, the first indication information determination module 1140 may be configured to determine indication information capable of being reflected on a surface of the target object through an indication device based on the operation guidance information.

In some embodiments, the operation guidance information output module 1150 may be configured to output the operation guidance information through a terminal device.

In some embodiments, the system 1100 for determining the operation guidance information may further include a second indication information determination module configured to determine the indication information capable of being reflected on the surface of the target object based on the orientation information and/or the spatial location information and the operation guidance information.

It should be understood that the system and modules thereof in FIG. 11 may be implemented in various ways. For example, in some embodiments, the system and modules thereof may be implemented by hardware, software, or a combination of software and hardware. The hardware part may be implemented by using a dedicated logic; and the software part may then be stored in a memory and executed by an appropriate instruction execution system, such as a microprocessor device or specially designed hardware. Those skilled in the art will appreciate that the method and the system described above can be implemented using computer-executable instructions and/or contained in processing device control codes, for example on a carrier medium such as a magnetic disk, CD or DVD-ROM, such as a programmable read-only memory (firmware) or on a data carrier such as an optical or electronic signal carrier. The system and modules thereof in the present disclosure may not only be implemented by hardware circuits such as very large scale integrated circuits or gate arrays, semiconductors such as logic chips, transistors, etc., or programmable hardware devices such as field programmable gate arrays, programmable logic devices, etc., may also be implemented by, for example, software executed by various types of processing devices, or may also be implemented by a combination (e.g., firmware) of the above hardware circuits and software.

It should be noted that the above description of the system for determining operation guidance information and modules thereof is only for convenience of description, and does not limit the present disclosure to the scope of the illustrated embodiments. It can be understood that for those skilled in the art, after understanding the principle of the system, it is possible to combine various modules arbitrarily, or form a subsystem to connect with other modules without departing from this principle. For example, in some embodiments, the optical image obtaining module 1110, the target part obtaining module 1120 and the operation guidance information determination module 1130 disclosed in FIG. 11 may be different modules in one system, or one module may implement the functions of the above-mentioned two or more modules. As another example, the first indication information determination module 1140 may be omitted. As another example, the operation guidance information output module 1150 may also be omitted. As another example, the second indication information determination module may also be omitted. As another example, two or more modules may share one storage module, or each module may have its own storage module. Such deformations are within the protection scope of the present disclosure.

The possible beneficial effects of the embodiments of the present disclosure include but are not limited to the following contents. (1) The operation location of the target part and/or the location of the lesion on the target part corresponding to the surface of the target object may be determined accurately by a combination of the optical image and the medical image. (2) Optical images and medical images may be used to train machine learning models, and the location of the surgical operation can be accurately located without completely relying on the doctor's experience. (3) The operation guidance information can be output through the terminal equipment, so that the doctor can find the location and the trajectory of the operation more intuitively for operation, and the efficiency of the operation of the doctor can be improved. It should be noted that different embodiments may have different beneficial effects. In different embodiments, the possible beneficial effects may be any one or a combination of the above, or any other possible beneficial effects.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

In addition, those skilled in the art may understand that various aspects of the present disclosure may be illustrated and described in several patentable categories or circumstances, including any new and useful process, machine, product or substances, or any combination of them, or any new and useful improvements. Accordingly, all aspects of the present disclosure may be performed entirely by hardware, may be performed entirely by software (including firmware, resident software, microcode, etc.), or may be performed by a combination of hardware and software. The above hardware or software can be referred to as "data block", "module", "engine", "unit", "component" or "system". In addition, aspects of the present disclosure may appear as a computer product located in one or more computer-readable media, the product including computer-readable program code.

A non-transitory computer storage medium may include a propagated data signal embodying a computer program code, for example, in baseband or as part of a carrier wave. The propagated signal may have various manifestations, including electromagnetic form, optical form, etc., or a suitable combination. The non-transitory computer storage medium may be any computer-readable medium, other than a computer-readable storage medium, that may be used to communicate, propagate, or transfer a program for use by being coupled to an instruction execution system, apparatus, or device. Program codes residing on the computer storage medium may be transmitted over any suitable medium, including radio, electrical cables, optical fiber cables, RF, or the like, or a combination of any of the foregoing.

The computer program codes required for the operation of each part of the present disclosure may be written in any one or more programming languages, including object-oriented programming languages such as Java, Scala, Smalltalk, Eiffel, JADE, Emerald, C++, C#, VB.NET, Python etc., conventional procedural programming languages such as C language, Visual Basic, Fortran 2003, Perl, COBOL 2002, PHP, ABAP, dynamic programming languages such as Python, Ruby and Groovy, or other programming languages, etc. The program codes may run entirely on the user's computer, or as a stand-alone software package, or run partly on the user's computer and partly on a remote computer, or entirely on the remote computer or server. In the latter case, the remote computer may be connected to the user computer through any form of network, such as a local area network (LAN) or wide area network (WAN), or to an external computer (e.g., through the Internet), or in a cloud computing environment, or as a service such as software as a service (Saas).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the present disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. Although the above disclosure discusses through various examples what is currently considered to be a variety of useful embodiments of the present disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments.

Similarly, it should be appreciated that in the foregoing description of embodiments of the present disclosure, various features are sometimes grouped together in a single embodiment, figure, or description thereof for the purpose of streamlining the present disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

Figure 12:
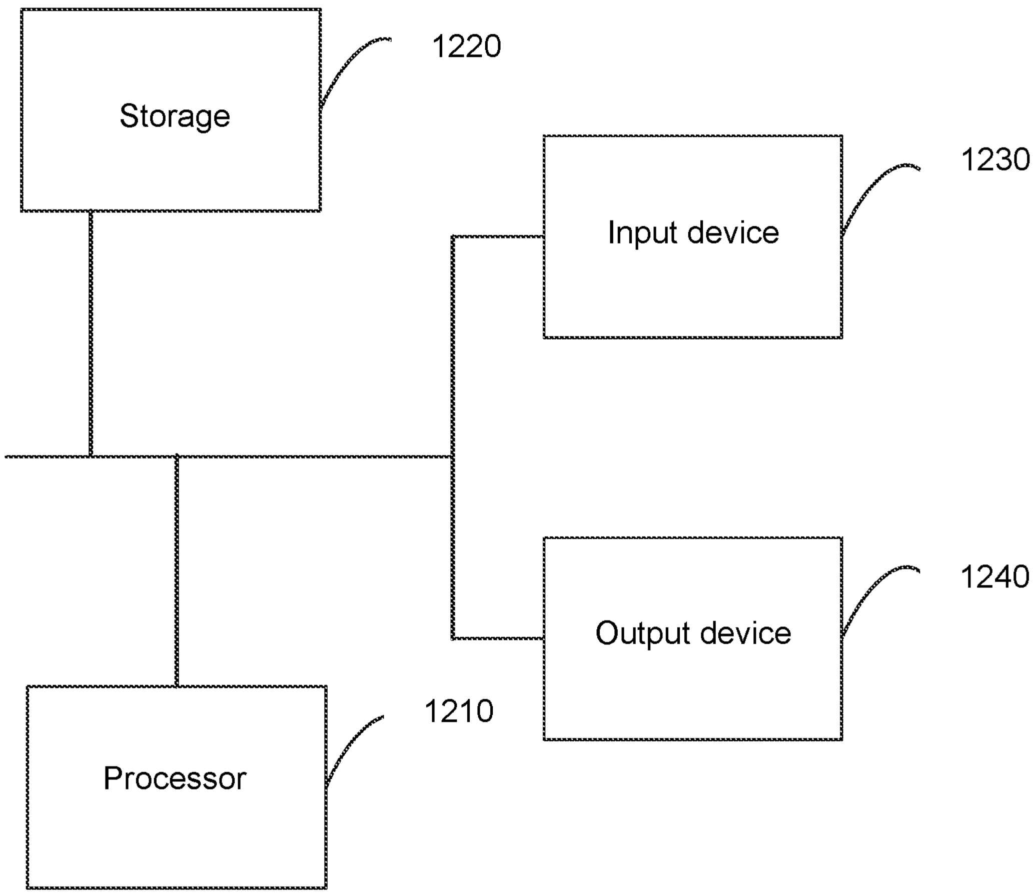
FIG. 12 is a schematic structural diagram illustrating an imaging device according to some embodiments of the present disclosure.

FIG. 12 is a schematic structural diagram illustrating an imaging device according to some embodiments of the present disclosure. As shown in FIG. 12, the device may include a processor 1210, a storage 1220, an input device 1230, and an output device 1240. There may be one or more processors 1210 in the device. One processor 1210 may be taken as an example in FIG. 12. The processor 1210, the storage 1220, the input device 1230, and the output device 1240 in the device may be connected through a bus or in other ways. In FIG. 12, connection through the bus is taken as an example.

The storage 1220, as a computer-readable storage medium, may be used to store software programs, computer-executable programs, and modules, such as program instructions/modules (e.g., the image obtaining module 1010, the image fusion module 1020, and the path planning module 1030 in the device for path planning device) corresponding to the method for path planning in some embodiments of the present disclosure. The processor 1210 may execute various functional applications and data processing of the device by running software programs, instructions and modules stored in the storage 1220, to implement the above theme update method.

The storage 1220 may mainly include a program storage region and a data storage area. The program storage region may store an operating system and an application program required by at least one function. The data storage region may store data created based on the use of the terminal, or the like. In addition, the storage 1220 may include a high-speed random access memory. The storage 1220 may also include a non-volatile storage, such as at least one magnetic disk storage device, a flash memory device, or other non-volatile solid-state storage devices. In some instances, the storage 1220 may further include storages set remotely relative to the processor 1210, and these remote storages may be connected to the device through the network. Examples of the aforementioned network may include, but not limited to, the Internet, an intranet, LAN, a mobile communication network, or a combination thereof.

The input device 1230 may be configured to receive input number or character information, and generate key signal input relating to user setting and function control of the device. The output device 1240 may include a display device such as a display screen.

The embodiments of the present disclosure further provide a storage medium containing computer-executable instructions. The computer-executable instructions may be used to execute the method for path planning when the computer-executable instructions are executed by a computer processor. The method may comprise the following operations.

An X-ray image of a target object may be obtained, and a location of a lesion may be marked on the X-ray image of the target object;

An ultrasonic image of the target object may be obtained, and a fused image may be obtained by fusing the ultrasonic image of the target object with the marked X-ray image; and A planned path may be obtained by performing a path planning based on a location of the lesion in the fused image.

The present disclosure provides a storage medium containing computer-executable instructions. The computer-executable instructions may not be limited to the above-mentioned method operations, and may also execute the operations in the method for path planning in any embodiment of the present disclosure.

In closing, it should also be noted that in the present disclosure, relational terms such as first and second etc. are only intended to distinguish one entity or operation from another, and do not necessarily require or imply any such actual relationship or order between these entities or operations. Furthermore, the term "comprising", "including" or any other variation thereof is intended to cover a non-exclusive inclusion such that a process, method, article, or apparatus comprising a set of elements includes not only those elements, but also includes elements not expressly listed, or other elements inherent in the process, method, article, or device. Without further limitations, an element defined by the phrase "comprising a . . . " does not exclude the presence of additional identical elements in the process, method, article, or apparatus comprising the element.

Each embodiment in the present disclosure is described in a progressive manner, each embodiment focuses on the difference from other embodiments, and the same and similar parts of each embodiment can be referred to each other.

The above description of the disclosed embodiments is provided to enable those skilled in the art to make or use the present disclosure. Various modifications to these embodiments may be readily apparent to those skilled in the art, and the general principles defined herein may be implemented in other embodiments without departing from the spirit or scope of the present disclosure. Accordingly, the present disclosure may not be limited to the embodiments herein, but conform to the widest scope consistent with the principles and novel features disclosed herein.

What is claimed is:

1. A detection device configured to obtain an X-ray image and an ultrasonic image, comprising a housing and an X-ray detector accommodated in the housing, wherein the detection device further includes an ultrasonic detector accommodated in the housing, and the ultrasonic detector is capable of moving to a position not blocking the X-ray detector from receiving X-rays, wherein the X-ray detector is configured to move, in the housing, along a first direction perpendicular to a panel surface of the housing where a tissue to be detected is placed, the ultrasonic detector is configured to move, in the housing, along a second direction parallel to the panel surface, and when X-ray detection is performed on the tissue to be detected, the ultrasonic detector moves along the second direction in the housing to a position fit to an inner wall of the housing such that the ultrasonic detector is moved out of the detection surface of the x-ray detector, and the X-ray detector is moved along the first direction to be close to the panel surface, and when ultrasonic detection is performed on the tissue to be detected, the X-ray detector moves along the first direction in the housing away from the panel surface such that a space is formed between the panel surface of the housing and the X-ray detector allowing the ultrasonic detector to move along the second direction.

2. The detection device of claim 1, wherein a groove is arranged on an inner surface of the ultrasonic detector close to the housing, and the groove is used to accommodate an ultrasonic couplant.

3. The detection device of claim 1, wherein the first direction is a vertical direction and the second direction is a horizontal direction, the detection device further comprising:

a first slide rail arranged along the horizonal direction; and a second slide rail arranged in the vertical direction on the housing, wherein the first slide rail is arranged on the housing, the first slide rail is arranged between the panel surface of the housing and the X-ray detector, the second slide rail is arranged in an accommodation space of the housing, and the ultrasonic detector is slidably arranged on the first slide rail, and the X-ray detector is slidably arranged on the second slide rail.

4. The detection device of claim 3, wherein a plurality of clamping structures are arranged at intervals on the second slide rail, and the plurality of clamping structures limit a location of the X-ray detector on the second slide rail and limit a distance of the X-ray detector relative to the panel surface of the housing.

5. The detection device of claim 1, wherein the X-ray detector is configured to move, in the housing, in a vertical direction relative to the panel surface of the housing and the ultrasonic detector is configured to move, in the housing, along a horizontal direction.

6. The detection device of claim 1, further including: an independent movement mechanism arranged in the housing, wherein the independent movement mechanism is connected with both the ultrasonic detector and the X-ray detector to control the ultrasonic detector and the X-ray detector to move independently or simultaneously.

7. The detection device of claim 1, wherein the independent movement mechanism includes a three-axis motion device.

8. The detection device of claim 7, further including a scraping device, wherein the scraping device is slidably arranged on the panel surface of the housing, and the scraping device is configured to scrape an ultrasonic couplant left on the panel surface of the housing.

9. The detection device of claim 8, wherein the scraping device is arranged along a width direction of the panel surface of the housing, and a surface of the scraping device in contact with the panel surface of the housing is a silicone material.

10. The detection device of claim 8, further including a storage device, wherein the storage device is arranged on one side of the housing, and the storage device is configured to store the ultrasonic couplant scraped by the scraping device.

11. The detection device of claim 1, wherein the panel surface of the housing is parallel to a detection surface of the X-ray detector, and X-rays enter the detection surface of the X-ray detector through the panel surface of the housing.

12. The detection device of claim 11, wherein a vertical distance between the panel surface of the housing and the X-ray detector is adjusted by moving the X-ray detector along the first direction perpendicular to the panel surface.

13. The detection device of claim 11, wherein the ultrasonic detector slides on an inner side of the panel surface of the housing in an accommodation space of the housing.

14. A detection device configured to obtain an X-ray image and an ultrasonic image, comprising:
a housing,
an X-ray detector and an ultrasonic detector accommodated in the housing, wherein the detection device further includes a movement mechanism connected with the ultrasonic detector and the X-ray detector to control the ultrasonic detector and the X-ray detector to move independently or simultaneously, the movement mechanism includes a three-axis motion device configured to control the ultrasonic detector to move, in the housing, along a horizontal direction parallel to a panel surface of the housing where a tissue to be detected is located, and the X-ray detector to move, in the housing, along a vertical direction perpendicular to the panel surface of the housing, and
wherein when X-ray detection is performed on the tissue to be detected, the ultrasonic detector moves along the horizontal direction in the housing to a position fit to an inner wall of the housing such that the ultrasonic detector is moved out of the detection surface of the x-ray detector, and the X-ray detector is moved along the vertical direction to be close to the panel surface.

15. A detection device configured to obtain an X-ray image and an ultrasonic image, comprising:
a housing,
an X-ray detector and an ultrasonic detector accommodated in the housing, wherein the detection device further includes a first slide rail arranged in an accommodation space of the housing along a horizontal direction and a second slide rail arranged in the accommodation space of the housing along a vertical direction, wherein the ultrasonic detector is slidably arranged on the first slide rail, and the X-ray detector is slidably arranged on the second slide rail, the X-ray detector is a flat panel detector and
wherein when X-ray detection is performed on the tissue to be detected, the ultrasonic detector moves along the horizontal direction in the housing to a position fit to an inner wall of the housing such that the ultrasonic detector is moved out of the detection surface of the x-ray detector, and the X-ray detector is moved along the first direction to be close to the panel surface, and
when ultrasonic detection is performed on the tissue to be detected, the X-ray detector moves along the vertical direction in the housing away from the panel surface such that a space is formed between the panel surface of the housing and the X-ray detector allowing the ultrasonic detector to move along the horizontal direction.

* * * * *